US006852288B2

(12) United States Patent
Newberg

(10) Patent No.: US 6,852,288 B2
(45) Date of Patent: Feb. 8, 2005

(54) SYSTEM FOR MULTIPLE STERILE SAMPLE COLLECTION AND ISOLATION

(75) Inventor: Douglas A. Newberg, Plainsboro, NJ (US)

(73) Assignee: NL Technologies, Ltd., Gambrills, MD (US)

(*) Notice: Subject to any disclaimer, the term of this patent is extended or adjusted under 35 U.S.C. 154(b) by 0 days.

(21) Appl. No.: 09/919,836

(22) Filed: Aug. 2, 2001

(65) Prior Publication Data

US 2002/0041830 A1 Apr. 11, 2002

Related U.S. Application Data

(60) Provisional application No. 60/222,610, filed on Aug. 2, 2000.

(51) Int. Cl.[7] .................................................. B01I 3/02
(52) U.S. Cl. ....................... 422/100; 422/102; 422/103; 422/104; 436/43; 436/47; 436/49; 436/180; 73/863; 73/863.95; 73/863.71; 73/864; 73/864.23
(58) Field of Search .......................... 422/100, 102–104, 422/26, 28; 436/43, 47, 49, 180; 73/863, 863.95, 863.71, 864, 864.23, 863.45

(56) References Cited

U.S. PATENT DOCUMENTS

| 3,383,923 | A | 5/1968 | Conche et al. |
| 4,170,798 | A | 10/1979 | Krumdieck |
| 4,526,045 | A | 7/1985 | Reekie |
| 4,662,231 | A | 5/1987 | Schaaraschmidt et al. |
| 5,409,841 | A | 4/1995 | Chow |
| 5,533,407 | A | 7/1996 | Besnier |

FOREIGN PATENT DOCUMENTS

EP              913465 A1 * 5/1999       ............ C12M/1/34

* cited by examiner

Primary Examiner—Jill Warden
Assistant Examiner—LaToya I. Cross
(74) Attorney, Agent, or Firm—Birch, Stewart, Kolasch & Birch, LLP

(57) ABSTRACT

This device is directed at filling multiple receptacles without losing integrity of the system. It is also directed at receiving a (sealed) container of receptacles (opened or stopper/closed), opening an access into the sealed container, retrieving receptacles, filling those receptacles, stoppering the receptacles after filling and ejecting the receptacles, either directly into the outside environment or into a closable sack or container, in the latter case while maintaining the integrity of the environment within the device and, if desirable, the sack or closed container.

20 Claims, 11 Drawing Sheets

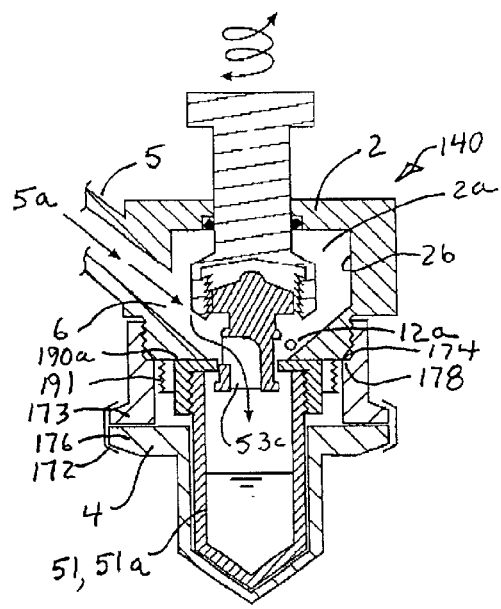
FIG. 7
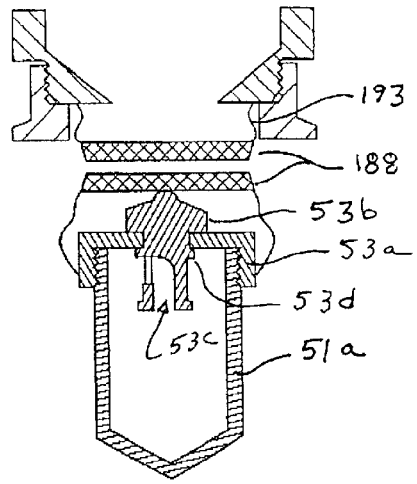
FIG. 8
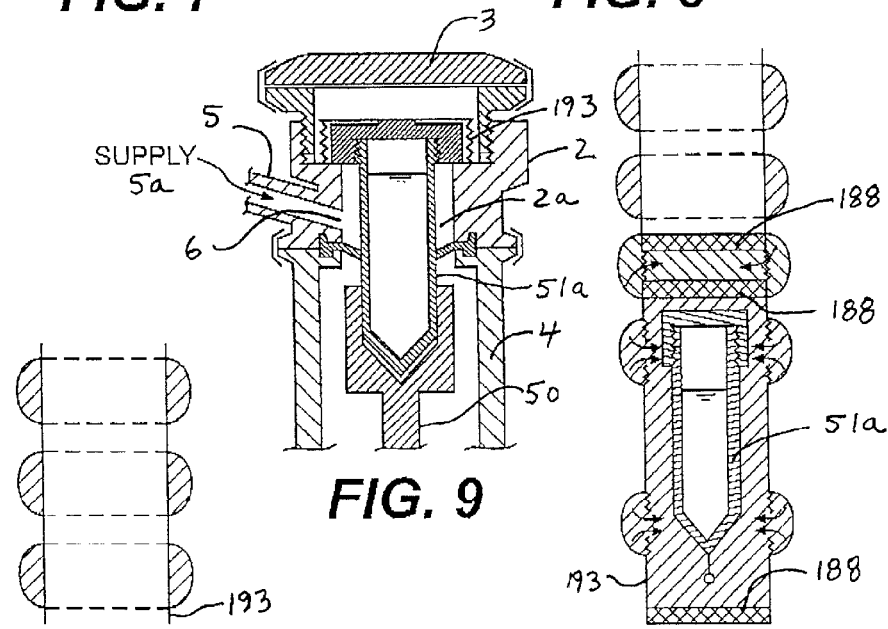
FIG. 9
FIG. 10A
FIG. 10B

SYSTEM FOR MULTIPLE STERILE SAMPLE COLLECTION AND ISOLATION

This application claims priority on provisional Application No. 60/222,610 filed on Aug. 2, 2000, the entire contents of which are hereby incorporated by reference.

BACKGROUND OF THE INVENTION

1. Field of the Invention

The present invention is directed to a system for multiple sterile sample collection and isolation. In particular, the present invention is directed to a sample collection apparatus, wherein a sample can be taken from within a sealed housing, while the sample and the inside of the housing are isolated from the outside ambient environment.

2. Description of Background Art

The pharmaceutical and biotechnology industry, the food and beverage industry, and the industrial enzyme and chemical industries all use processes that are conducted to a greater or lesser degree in isolation from the surrounding environment. While instrumentation exists for in-situ monitoring of many variables of a process, the monitoring of some variables still requires that physical samples be removed from the process for analysis elsewhere. It is frequently desirable that these samples be obtained without exposing the surrounding environment to the process, without exposing the sample material to the technician or the surrounding environment, or some or all of the above. One example of a case involving the desire to isolate the process, the surrounding environment, the technician and the sampled process material (once removed from the process) all isolated from each other is in the production of some toxic and hazardous chemotherapeutic agents or vaccines. The invention described herein provides a means through which such sampling can be accomplished. It should be understood that not all of the features of the system described need to be applied or incorporated into the system for it to be essentially the same system since, to have read this description and to have eliminated elements not necessary in a given application would be obvious to one knowledgeable in the field.

SUMMARY OF THE INVENTION

The present invention is directed to a device for sampling, wherein it is possible to isolate the process, the surrounding environment, the technician and/or the sampled process material in a simplified and more complete manner than the in the background art. In order to accomplish the above, the present invention provides a housing with an internal cavity containing a mechanism or set of mechanisms for maneuvering a single or multiple receptacles to a position where material may be filled into them before they are stopped or otherwise closed. The housing may mate with one or more containers holding one or more unfilled receptacles, which can be transferred into the housing to be filled. The housing and the mating surfaces between the housing and the container (or containers) may be cleaned, sterilized or otherwise decontaminated before the environment within the housing and the container holding the unfilled receptacles are brought into communication with each other, while being kept segregated from the outside surrounding environment. Likewise, the housing may mate with one or more closable containers capable of receiving one or more filled receptacles such that, once inside the container, the receptacles may be removed from the housing without exchange occurring between the environment within the container holding the filled receptacle, and the outside ambient environment. The housing and the mating surfaces between the housing and the container for receiving the filled receptacles may be cleaned, sterilized or otherwise decontaminated before the environment within the housing and the container for receiving the filled receptacles are brought into communication with each other while being kept segregated from the outside surrounding environment.

A primary object of the present invention is to receive one or more clean receptacles prepackaged in a clean outer package or container equipped with an access port which can be form a seal with the device and through which the clean receptacles can be transferred to be filled. Once filled, the receptacles can be removed through a second port (or through the same port, particularly if only one receptacle or group of receptacles is involved) into a package which can then be removed from the device while preserving the integrity of the environment within the device and within the package containing the receptacles from the ambient environment outside of the device.

Another primary object of the present invention is to provide a device which is capable of carrying out multiple material transfers from a source to a receptacle, wherein an exchange between the environment where the transfer takes place and the outside ambient environment can be largely inhibited.

Yet another primary object of the present invention is to provide a device, wherein the transfer can be made and the individual receptacles be stoppered before the housing is reopened. Furthermore, exchange between the environment within the invention and containing the filled, stoppered receptacles is prevented from exchange with the outside ambient environment.

Still another primary object of the present invention is to provide a series of steps by which empty receptacles may be filled and stoppered without exposing the ambient environment to the environment where the receptacles are filled.

Another object of the present invention is to provide a device by which exchange between the environment within the device and the outside ambient environment can be inhibited.

Another object of the present invention is to enable an operator to collect a single or multiple samples into individual unstoppered or stoppered receptacles and to seal the receptacles and package them individually or in groups. Furthermore, the packaged receptacles can be removed from the system without breaking the system's containment integrity from the surrounding environment or with the source of the material being filled into the receptacles.

The system according to the present invention can be used to transfer large volumes of material into smaller packages (vials, bottles, bags, etc.) and to place the packages into a secondary package, wherein material released during the filling operation and resting on the primary container can be sealed and be kept isolated from the surrounding environment when the secondary package containing the primary container filled with the material is detached from the system.

In the device and system according to the present invention, it is possible to collect samples of various types of materials that are capable of flowing. Accordingly, samples materials can be liquids, solids or gases.

The system may include a valved feed port for feeding a material into the interstitial space between the primary container or receptacle and the secondary package or bag in order to neutralize any toxic or hazardous materials resident on the primary container or within the secondary package.

The system may be fitted with a $2^{nd}$ feed line which will direct material (such as a preservative or neutralizing agent, for example) into the primary container at the filling station before, during or after the primary container is filled but before it is recapped.

It should be noted that although the device of the present invention is designed for filling and sealing containers in a contained fashion, the system might be operated in an opened fashion.

In addition, all feed lines, vents and drains may be valved. Accordingly, when taken in combination with the sealed housing and the gasketed septum at the mouth of a bag or container from which empty primary receptacles are fed into the system and the gasketed septum at the mouth of a bag or container into which the filled primary receptacles are ejected, the system is a closed system from the outside surrounding environment. Accordingly, the entire process of sampling can be performed within a closed system.

The system according to the present invention includes a corer to core the septa sealing mouths of the bags or containers for holding the empty and filled receptacles, allowing them to open into the housing interior.

The system of the present invention includes a primary container clasp assembly, which can be lowered to capture the primary container, in this case, a receptacle. When raised, this assembly brings the receptacle stopper into contact with a stopper clasp assembly. When rotated, the combination of the primary container clasp assembly and the stopper clasp assembly can hold the receptacle still while the stopper is rotated off. The receptacle can then be lowered under the feed ports and filled. The stopper can then be replaced by reversing the process.

The system of the present invention also includes an ejector rod, which can be used to push the filled primary container out of the ejection port. This rod can be rotated, raised and lowered.

Although not shown, a similar injector rod can be included to capture the first (or any) unfilled primary container and bring it up to a position where the primary container clasp may engage it.

The system of the present invention may be cleaned and sterilized in place and may be made to be maintained and operated under pressure or under vacuum.

Further scope of applicability of the present invention will become apparent from the detailed description given hereinafter. However, it should be understood that the detailed description and specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The present invention will become more fully understood from the detailed description given hereinbelow and the accompanying drawings which are given by way of illustration only, and thus are not limitative of the present invention, and wherein:

FIG. 7 is a cross-section of an alternative embodiment of the device of the present invention, wherein single receptacles may be filled and removed from the environment in which they were filled without allowing exchange between the outside ambient environment and the environment within the device where the receptacle was filled or the environment within the closed container holding the filled receptacle;

FIG. 8 is a cross-section of the device shown in FIG. 5 with the plunger in the stopper of the filled receptacle depressed into a closed position, the lower portion of the housing removed, the receptacle tube sack extended and sealed over the upper material exposed portion and separated from the housing to which the upper portion of the sealed receptacle tube sack remains attached;

FIG. 9 is a cross-section of an alternative embodiment, wherein an individual receptacle can be attached to a housing for filling and the filled receptacle can be removed from the housing through the top of the housing rather than through the bottom of the housing as is illustrated in FIGS. 5 and 6;

FIGS. 10A and 10B are cross-sections of alternative embodiments of the present invention.

DESCRIPTION OF THE PREFERRED EMBODIMENTS

Figure 1A:
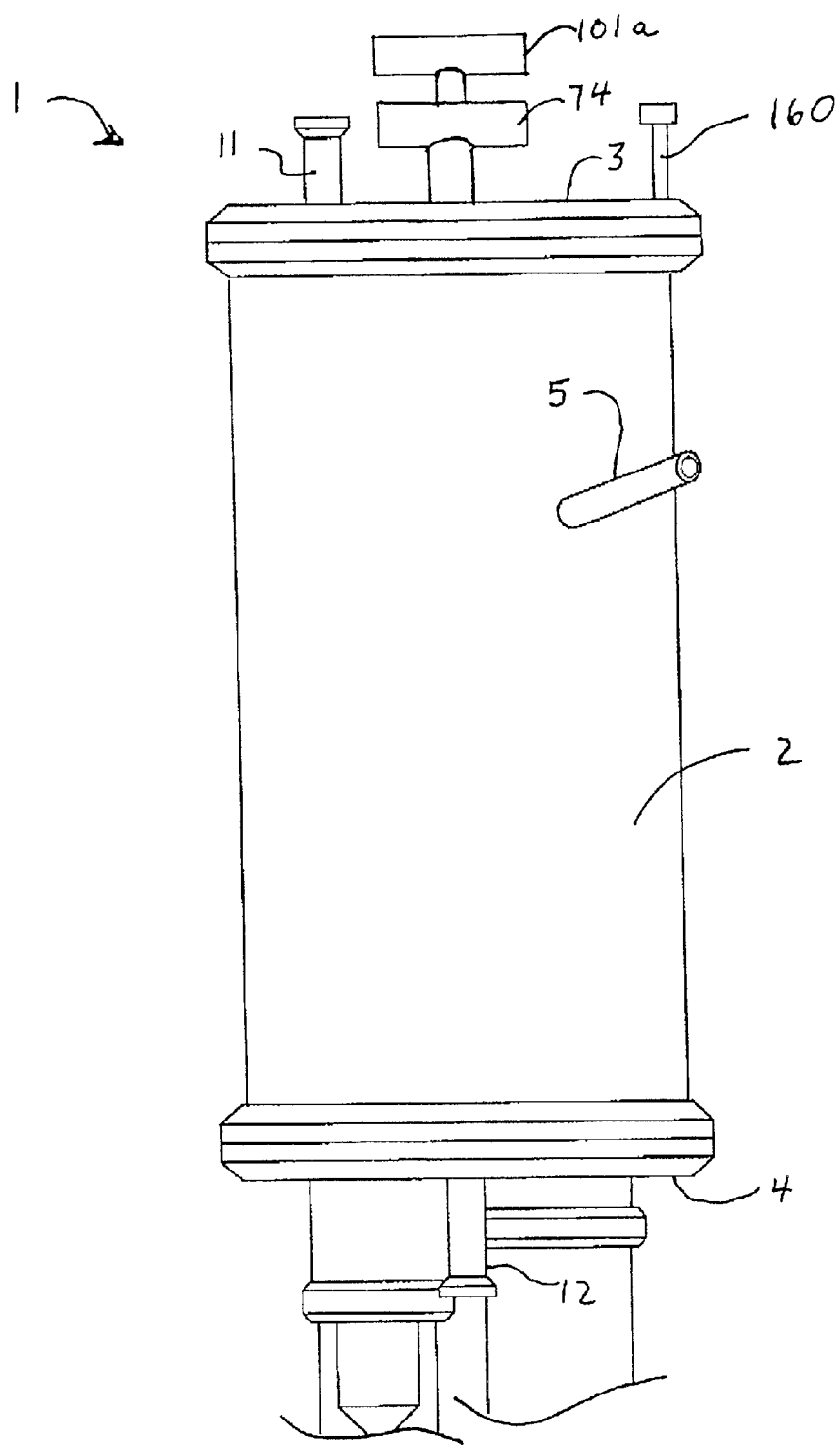
FIGS. 1A and 1B are side views of the outside of one embodiment of the device of the present invention.
Figure 1B:
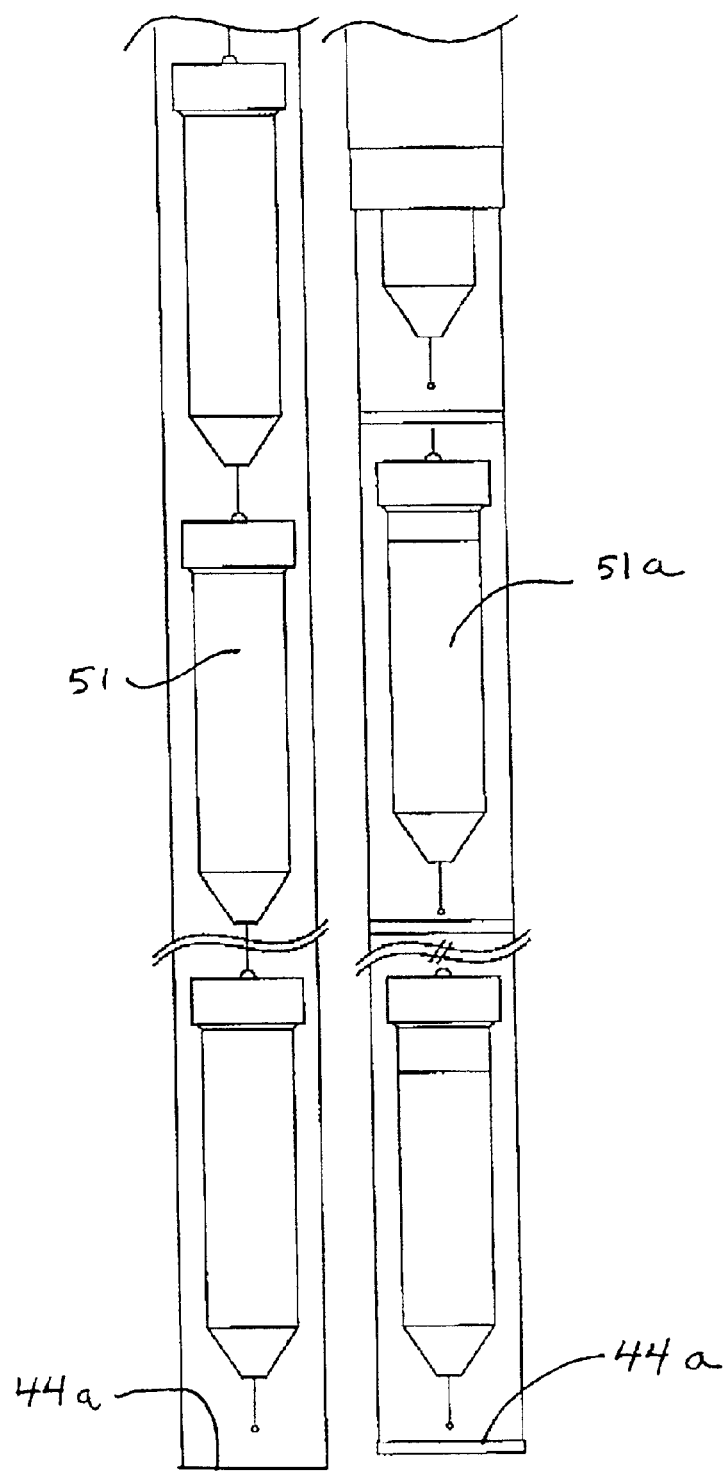

The present invention will now be described with reference to the accompanying drawings. It should be noted that the same references have been used throughout the several views to identify the same or similar elements.

The Main Housing:

Referring to FIGS. 1A, 1B and 2A–2D, the device of the present invention includes a main housing 2 with an internal cavity 2a. The housing is depicted as having a removable cover plate 3 and a base plate 4. The removable cover plate 3 and base plate 4 include flanges 21 and 24, respectively. Furthermore, the main housing 2 includes an upper flange 22 and a lower flange 23, which mate with the flanges 21 and 24 of the cover plate 3 and base plate 4, respectively. Furthermore, the lower surface 21a of the flange 21 of cover plate 3 is sealed with the upper surface 22a of flange 22 of main housing 2 by a gasket 3a, and the upper surface 24a of flange 24 of base plate 4 is sealed with the lower surface 23a of flange 23 of main housing 2 by a gasket 4a. The main housing 2 is removably attached to the cover plate 3 and base plate 4 using sanitary clamps 14 and 15, respectively.

Although the cover plate 3 and base plate 4 are illustrated as plates attached using sanitary clamps 14 and 15, these elements could be attached by various other means of attachment. Furthermore, although the cover plate 3 and base plate 4 provide greater ease of access into the main housing 2, these elements may be formed as fixed parts of the main housing 2. In addition, should an alternate port or additional access port be desired, other ports may be formed in the main housing 2, depending on the application.

The main housing 2 has a supply port 5 for receiving flowable material therethrough. The supply port 5 is connected upstream to at least one source of flowable material supply 5a. Materials supplied through port 5 include materials intended to be filled into an open empty receptacle 51. Normally, opened receptacles are positioned under opening 6 of supply port 5 located within internal cavity 2a of housing 2 before the material supply 5a is turned on so that supplied material flows into the receptacle 51. Once enough material is collected (including what might be resident in the supply line from the source to the opening 6 of supply port 5), supply 5a may be turned off. It should be noted that supply port 5 may also be connected to a manifold 5b for controlling the feeding of various other materials. In this way, supply port 5 could also be used to supply various other materials into the main housing, including desiccating, fixing, cleaning and sterilizing agents as well as other materials. Alternatively, other ports may be introduced into the main housing 2 for the purpose of supplying materials to the main housing 2 in independent fashion. For example, although not required, supply port 7 illustrated in FIG. 2 is such a port and is intended to supply small amounts of fixative agent into the receptacle 51 before, during or after the receptacle is filled with material from the supply port 5 and before the receptacle is stoppered. Supply port 7 has an opening 8 within internal cavity 2a.

It should be noted that the supply port 5, supply port 7 and any other ports could also be used to supply materials to the housing as well as to draw materials out of the housing, such as in the case of a vent. In the embodiment illustrated in FIGS. 2A–2D; however, cover plate 3 is shown with a dedicated valved vent port 11 for venting purposes. Accordingly, it is unnecessary to provide a vent in the main housing 2. It should also be noted that an intent of the device of the present invention is to control untreated material from being directly exchanged with the ambient environment outside the housing. Accordingly, material vented or drained from the housing would normally pass through closed piping or tubing to point where the material would be treated before being release to the ambient environment. In some cases physical treatment, such as filtration or heat-treating may be sufficient while in other cases, chemical or physical chemical treatments may be necessary.

Figure 2A:
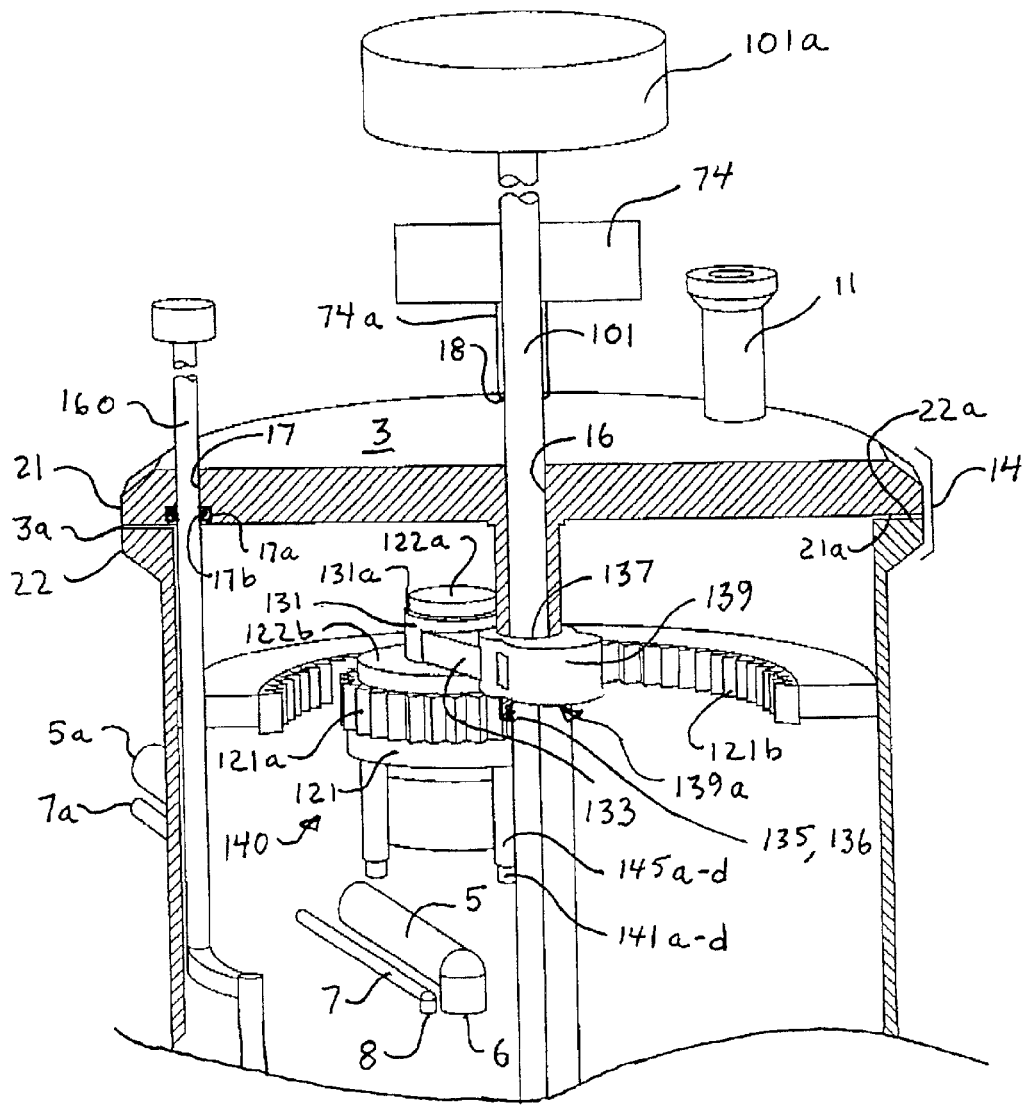
FIGS. 2A, 2B, 2C and 2D are vertical center cross sections through the device illustrated in FIG. 1.

Cover Plate:

Cover plate 3 in FIG. 2A includes a bore 16 with a tubular lower extension 19. A cam 139 (discussed later) is mounted for rotation on the tubular lower extension 19. A tube clasp manipulator rod 101 is mounted within the bore 16. The manipulator rod 101 is sealed with the bore 16 by an o-ring 135 and an o-ring grove 136 mounted within the walls of the bore 16 in a lower portion of the lower extension 19.

Cover plate 3 also includes a bore 17 through which a receptacle ejector rod 160 (discussed later) is mounted. Ejector rod 160 is sealed with the cover plate 3 by an o-ring 17a and an o-ring grove 17b located within the walls of the bore 17.

Additionally, cover plate 3 includes a bore 18 through which a coring rod 74a is mounted. Coring rod 74a is sealed with the cover plate 3 by an o-ring and groove combination 18a mounted in the wall of bore 18.

Although not illustrated in the above embodiments, the device of the present invention may be fitted with viewing windows in order to aid the operator with the use of the system.

Base Plate:

Base plate 4 may be attached to the bottom of the main housing 2 in a similar or alternative fashion to the cover plate 3. Likewise, either of the base plate 4 and cover plate 3 may be formed as a part of the main housing 2 while the other is detachable.

Figure 2B:
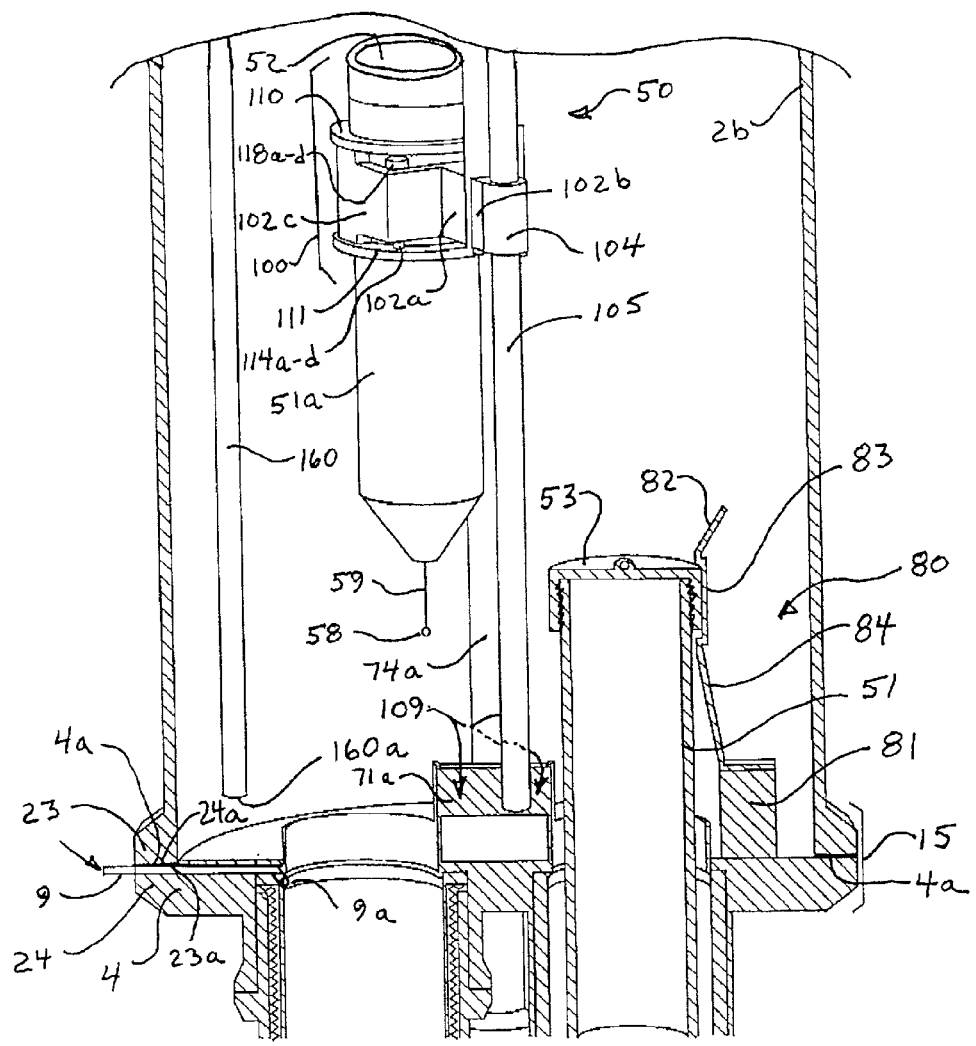
Figure 2C:
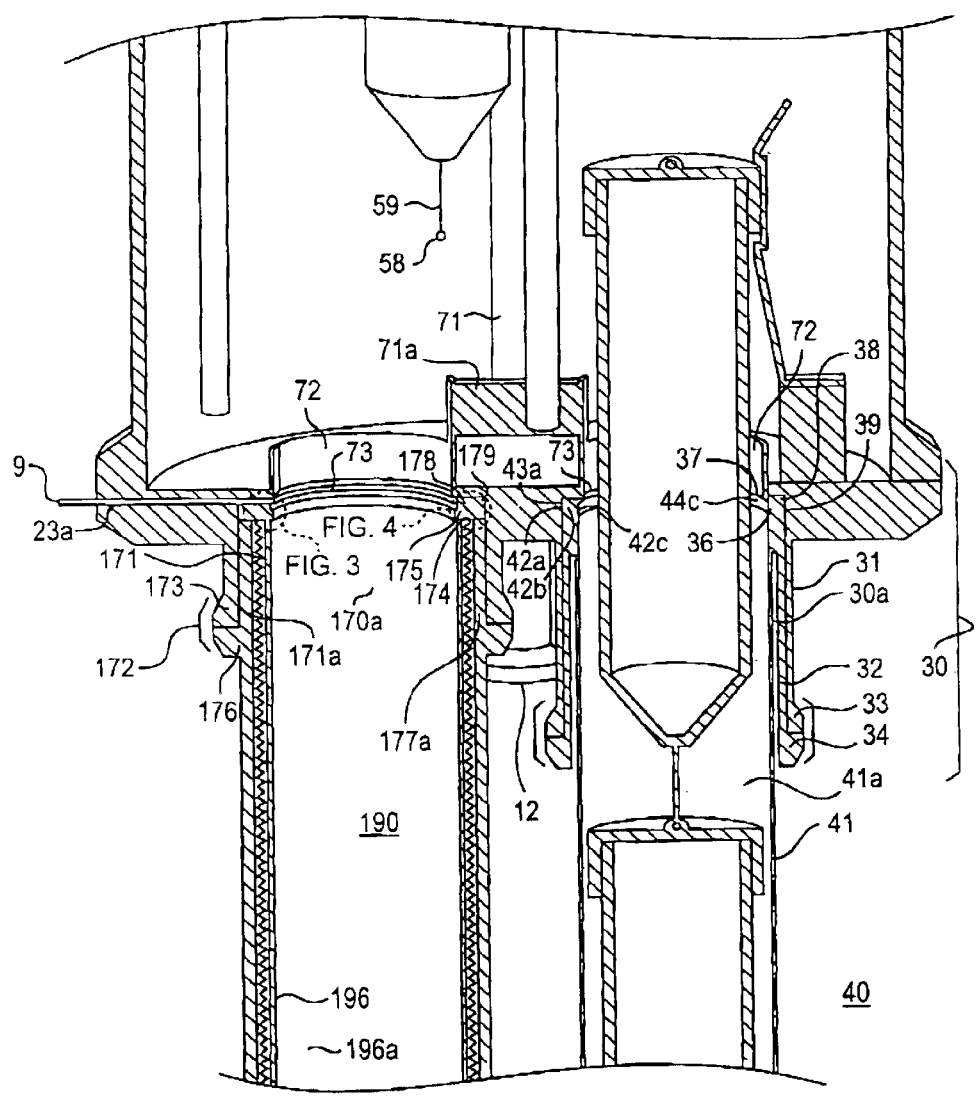

The base plate 4 illustrated in FIGS. 2B and 2C include three vertical through bores and one side bore. A drain opening (not visible) for valved drain port 12 is located at a lowest point so as to enhance drainage. Other bores include an injection bore 30a for receptacle injection port 30 and an ejection bore 170a for receptacle ejection port 170. A supply port 9 for adding a cleaning, disinfecting, sterilizing, neutralizing or otherwise decontaminating agent into portions of the receptacle tube sack before it is closed is shown. Supply port 9 has an opening 9a located in the base plate 4 above the septum 190a (discussed later) of the receptacle tube sack assembly 190 (also discussed later). It should be noted at this time that the elements of the device could be rearranged so that all of the openings currently illustrated in the cover plate could also be located in the base plate. Likewise, all of the openings that currently appear in the base plate could also be relocated in the cover plate with the exception of drain port 12, since the opening 12a should remain at the low point of the base plate.

It should be noted that although adding a cleaning, disinfecting, sterilizing, neutralizing or otherwise decontaminating agent through a supply port 9 and an opening 9a located within cover plate 3 would be more difficult (a tube feeding into a fold or lower section of the receptacle tube sack before it is sealed off would be one example), it can be accomplished and therefore should be considered to be within the scope of the present invention.

Figure 2D:
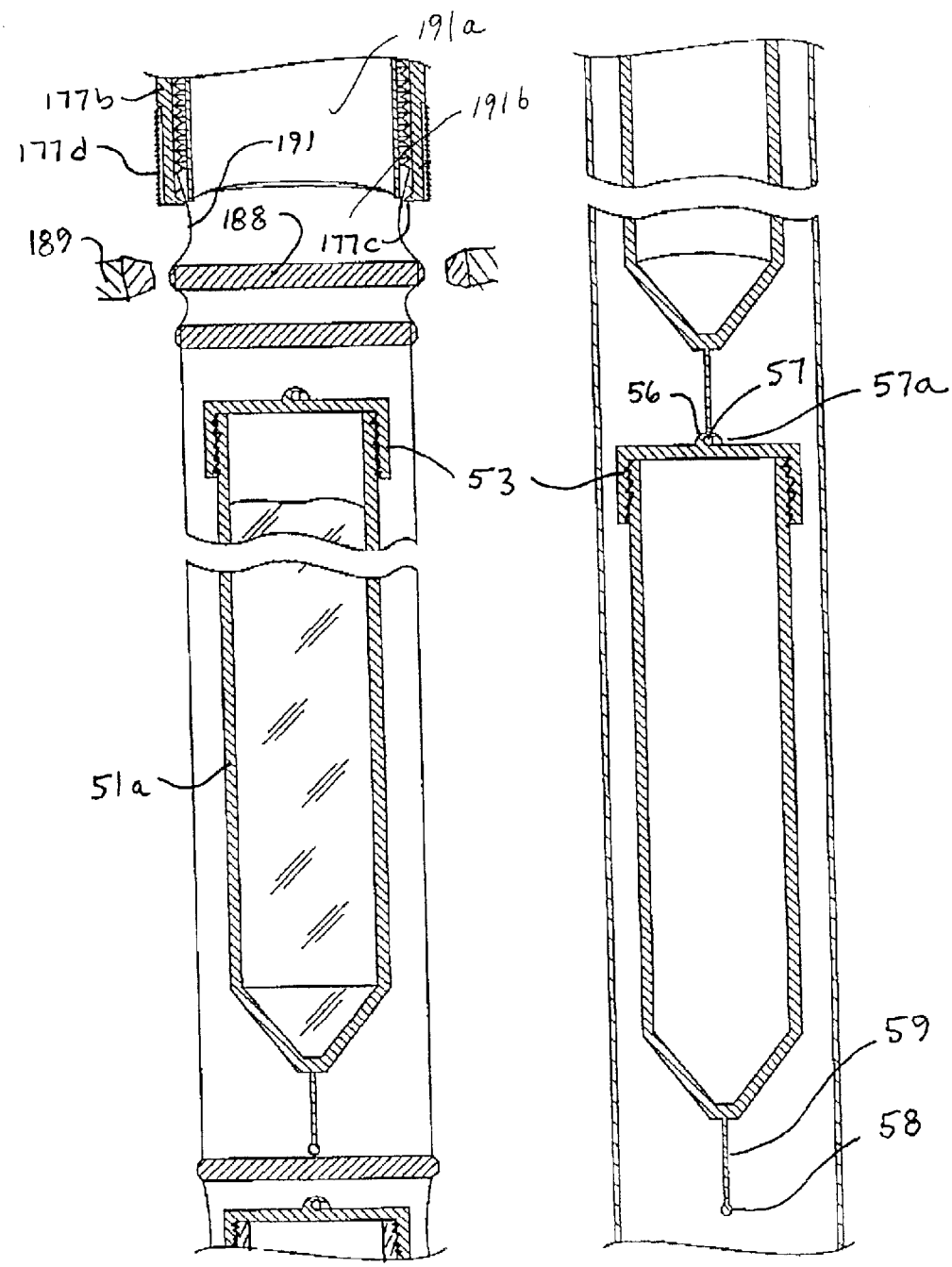

Injector Port Assembly:

Referring to FIGS. 2C and 2D, the injector port assembly will now be described. Injection port 30 includes an outer tubular section 31 that extends down beyond the bottom of the base plate 4 and is shown terminating in a sanitary clamp flange 33. Injection bore 30a is counterbored from the bottom up to form a seal face 36 relieved on the outer edge by an annular alignment recess 37 so that the internal bore of tubular section 31 is flush internally with the outside diameter wall of the alignment recess 37.

Insert 32 nests inside the inner bore of tubular section 31. The insert 32 includes a mirror image relieved seal face 38 with the outer edge also being relieved to form annular alignment recess 39. At the opposite end, insert 32 is shown with a sanitary clamp flange 34 that mates with flange 33. A sanitary clamp 46 is used to removably attach the sanitary flanges 33 and 34 to each other.

Receptacle Pack:

FIG. 2A–2D illustrate a device that is designed to accept single or multiple receptacles, to fill the receptacles and then to have the capacity to expel all of the receptacles without losing the integrity of the system relative to the surrounding ambient environment. In order to accomplish this an individual receptacle or a group of receptacles are prepackaged into an empty receptacle holder in the form of a receptacle package 40 or a receptacle magazine 40a (not shown). Although FIG. 2C illustrates the receptacles being completely enclosed in the receptacle package 40, it is only necessary that an access into the receptacle be enclosed in the package 40 such that, when the package is opened, the receptacle may be filled through the exposed access. Once filled, the access may be reclosed. In the case where the package 40 includes several receptacles, access to individual receptacles may be closed off after each receptacle is filled.

Additionally, FIGS. 2C and 2D shows the receptacles with screwed on stoppers in place. It should be noted that this illustrates only one of many possible types of stoppers that might be used and further illustrates only one of many way these stoppers may be affixed to the receptacles. Furthermore, it is not necessary that the supplied receptacles have stoppers fixed in place; receptacles may be supplied in the opened condition as well.

Figure 5:
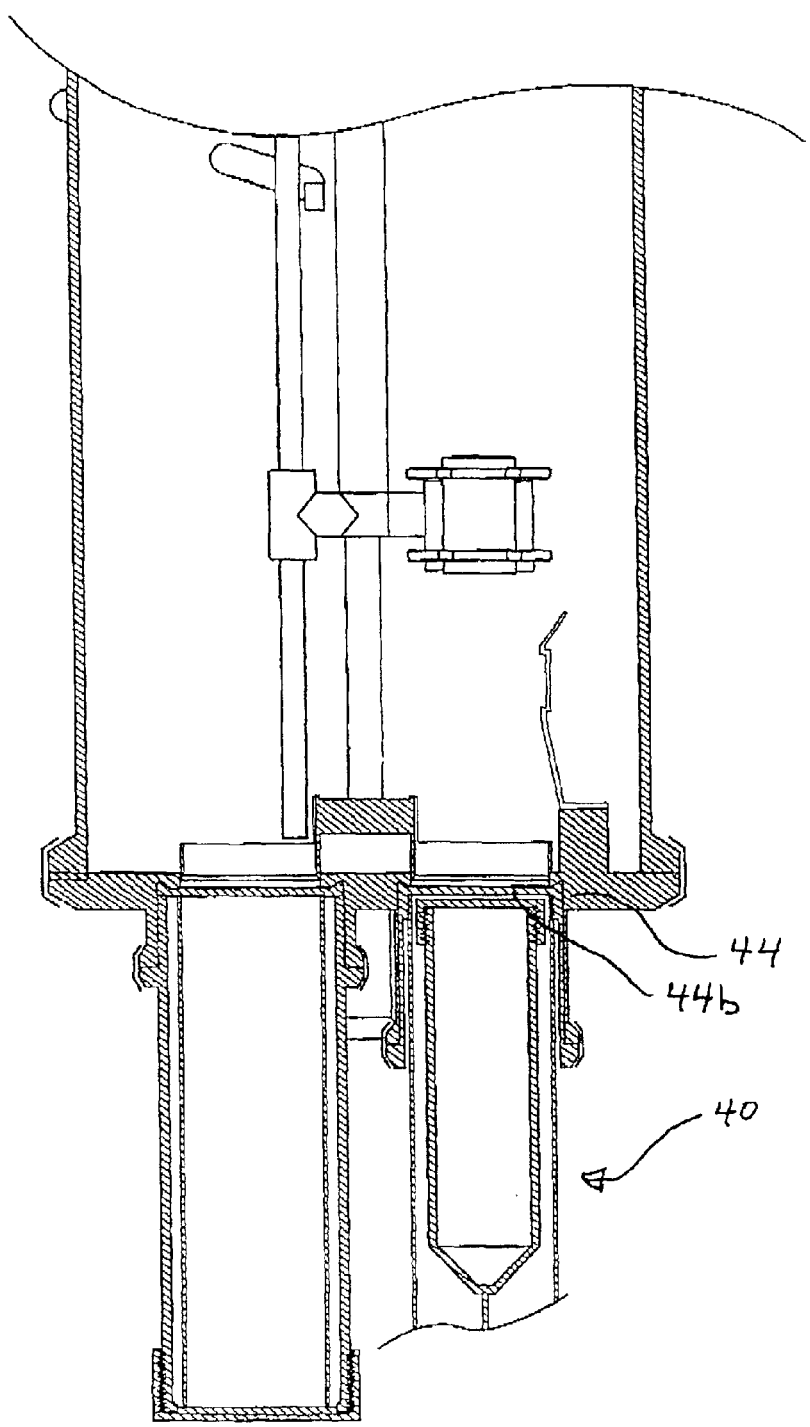
FIG. 5 is a vertical cross section of the lower half of the device shown in FIGS. 1A–2D illustrating the condition where a receptacle package (or receptacle pack) and a receptacle tube sack assembly are attached but not cored so as to bring the internal environments of the device, the receptacle pack and the receptacle tube sack assembly in communication with each other.

FIGS. 2C and 2D show receptacle package 40 as a flexible tubular structure with a tube wall 41 and a lumen 41*a* that is closed at both ends with flanged package septum 44 at the front end and terminating in a blind end 44*a* to the back of the receptacle package 40. Although the receptacle package 40 may have one or more receptacles which do not have to be pre-stoppered and do not have to be of any particular level of cleanliness or sterility, the receptacle package 40 illustrated in FIG. 2 is filled with several pre-stoppered receptacles stoppered with threaded stoppers. The stoppers' tops are each shown with a raised sprue 56, the sprue 56 having a hollow cavity 57 with a narrow slotted opening 57*a*. Receptacles are shown with bottoms tipped with a thread 59 ending in a blunt tip 58. The pre-stoppered receptacles are positioned linearly within lumen 41*a* in linked fashion head-to-toe (receptacle bottom tip to stopper top), similar to linked sausages. With the exception of the first stopper, pre-stoppered receptacles are linked to each other by having the blunt tip 58 of the receptacle inserted through the slotted opening 57*a* into the cavity 57 of the stopper that follows. The stopper of the first receptacle, shown in FIG. 5, is linked to the bottom of the septum 44 as will be described below.

Figure 3:
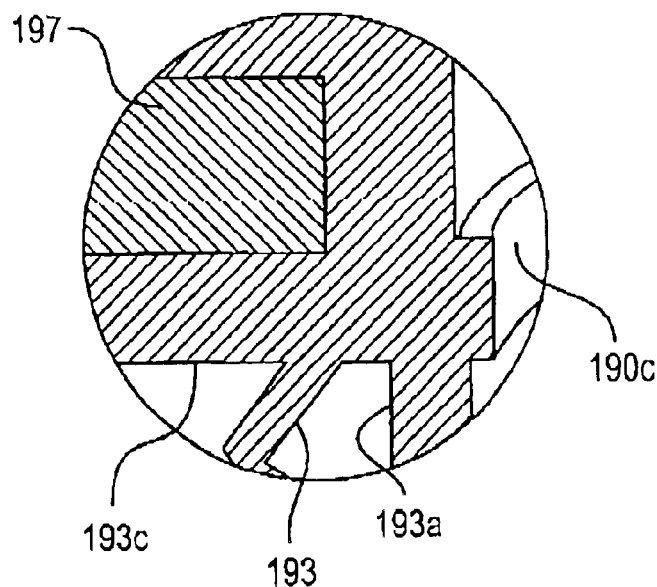
FIGS. 3 and 4 are detail views of portions 3 and 4 of FIG. 2C.
Figure 4:
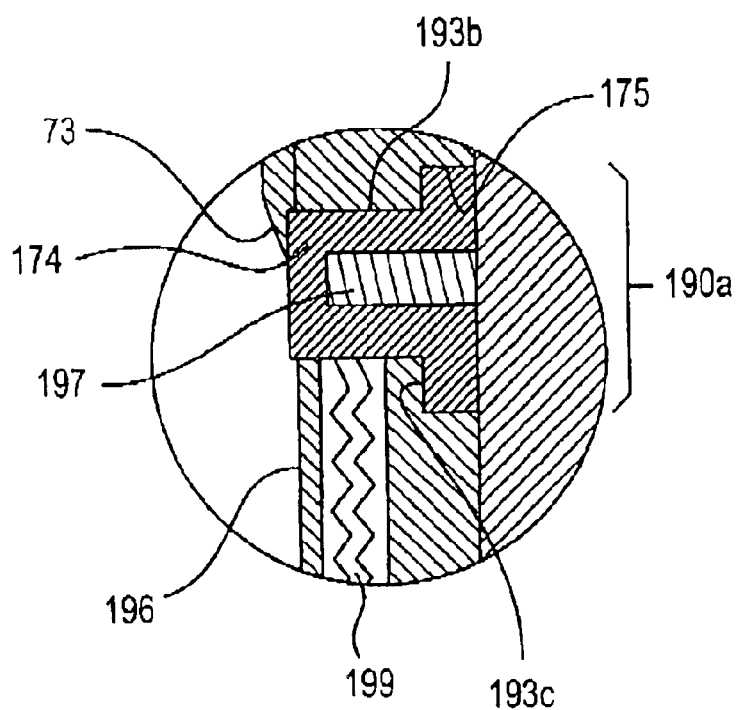

Continuing with FIG. 3, receptacle package 40 is shown topped by a flanged package septum 44 with sprue 56 of the first stopper affixed to a bottom surface thereof. Attaching the first stopper to the portion of the septum 44 which will later be cored exemplifies a method by which septum core 44*b* may be carried through the device and ejected on the other side as part of the first stopper, thus, removing it from the system and eliminating it as a possible mechanical hazard. This represents one manner in which to remove core 44*b* is prevented from interfering with later device operations. It should be understood that other methods of removal are possible but it also is not necessary to remove the core 44*b* from the system at all but, rather, simply position it or system components so as not to interfere with the system's operation.

In this embodiment the outer edge of the flanged portion of flanged package septum 44 extends above and below the adjacent inner radial portion 42*c* of the flange to form two short tubular sections 42*a* and 42*b*. When the flanged package septum 44 is inserted up through the internal bore 35 of insert 32 and insert 32 is itself inserted up into tubular section 31, tubular sections 42*a* and 42*b* become nested in alignment recesses 37 and 39 as the upper and lower surfaces of radial portion 42*c* mate with seal surfaces 36 and 38. When sanitary clamp 46 is affixed to flanges 33 and 34, insert 32 is firmly clamped in place and flanged package septum 44 firmly fixed and sealed above and below.

Cleaning the Housing:

One of the values of the device of the present invention is that it can fill receptacles in an environment isolated from the ambient surrounding environment. This device has particular value in processes where hazardous materials are handled and preventing release to the ambient environment is critical. Furthermore, the device of the present invention is valuable when obtaining uncontaminated samples from a process are important of where both of the above are important. The device of the present invention is also of value in other instances where sampling or subdividing, mixing or combining material in isolation is important.

Although the receptacles and their stoppers may be protected from the outside ambient environment and remain uncontaminated when prepackaged in a closed receptacle magazines 40 or receptacle tube sack assembly 190, the exterior of the receptacle package 40 and receptacle tube sack assembly 190 are exposed to the outside environment. Therefore, the exterior of the receptacle package 40 and receptacle tube sack assembly 190 are contaminated by the outside ambient environment. In the same way, the internal cavity 2*a* of the main housing 2, including the internal surfaces of each passage opening into the internal cavity 2*a* all the way back to the point where a closure or seal is formed, may become contaminated when exposed to the ambient environment. It is, therefore, standard practice to wash, clean, sterilize, neutralize or otherwise decontaminate the interior of the equipment once the equipment is assembled and closed to the outside ambient environment. Thus, once the receptacle package 40 and the receptacle tube sack assembly 190 are fixed in place and the housing is closed, washing, cleaning, sterilizing, neutralizing or other wise decontaminating agents may be applied to the interior of the system to wash, clean, sterilize, neutralize or other wise decontaminate the interior, including the upper surfaces of the flanged septa of receptacle package 40 and receptacle tube sack assembly 190, which are also exposed to the interior. Once this has been accomplished, coring of the septa can be carried out to open the lumen of the receptacle package 40 and of the receptacle tube sack assembly 190 and their contents to the inside cavity of main housing 2. Accordingly, the contents of the receptacle magazine and the receptacle tube sack assembly become part of the same isolated environment, separate from the outside surrounding ambient environment. Individual receptacles from the receptacle package 40 may be withdrawn from the package, conveyed into the internal cavity 2*a* of the main housing 2, unstoppered (if supplied in stoppered condition), filled, stoppered (if desired), ejected through the receptacle ejection port 170 and into the lumen 191*a* of the receptacle tube sack assembly 190 into the a blind section of tube sack 191*b*. As will be described later, a section of the tube wall 193 can be individually sealed and pinched off from the portion remaining attached and continuous with the internal cavity 2*a* of the main housing 2, allowing the integrity of the environment around the filled receptacle 51*a* and that of the internal cavity 2*a* to both be preserved separate from that of the surrounding ambient environment. If a hazardous material is being processed within the main housing 2, the main housing 2 may be washed, cleaned, sterilized, neutralized or otherwise decontaminated before being reopened to the ambient environment. In a similar fashion, a washing, cleaning, sterilizing, neutralizing or otherwise decontaminating material may be added to individual tube sacks before they are sealed off and separated from the environment within the housing. Alternatively, the individual section of tube sack may have incorporated in one or more pouches or spaces which may be released into the lumen of the tube sack once it is removed from the system, confining exposure to the agent only to the lumen of the tube sack holding the filled receptacle, keeping it separate from the internal cavity and connected environments.

Coring of the Septa:

The procedure for coring the septa will now be described. In this embodiment the receptacle injection port 30 and the receptacle ejection port 170 are both fitted with septa and both are cored at the same time. Since the coring procedure and the structure of the septa are similar for both the injection and ejection ports 30 and 170, the procedure will be described for the injection port 30 with the understanding that the same happens for the ejection port 170.

The coring assembly consists of an L-shaped coring rod 71, cross bar 71a and two cylindrical blades 72, each with 360° bottom cutting edges 73. The lower portion of one of the blades 72 rests in the upper portion of injection bore 30a while the lower portion of the other of the blades 72 rests in the counterpart upper portion of the ejection bore 170. As pressure is applied down on coring rod handle 74, coring rod 71 transfers the pressure through cross bar 71a and to the two blades 72, forcing their cutting edges 73 to core out a cylindrical core section of both the flanged package septum 44 and the flanged receptacle sack septum 190 (described later). Ridged or semi-ridged inserts 197 and 43a may be included in the structure to add rigidity to the septa in the area adjacent to where the cut is made. While the septum core 44b from the package septum 44 remains attached to the stopper of the first receptacle 51, the septum core 190b of the sack septum 190 will freely drop (or be pushed by the passage of the first filled receptacle 51a through the ejection port 170) into the lumen 191a of the receptacle tube sack assembly 190. Once cored, the opening through the septum 44 held in the injection port 30 and the septum 190 held in the ejection port 170 are both large enough so as to allow passage of receptacles or stoppers or receptacles with stoppers attached.

Instead of the vertical motion of the coring rod, the coring motion could be provided by extending cross bar 71a to mate with a rotating lever arm through the side wall of the housing. A cam on the lever arm could impart the motion to cross bar 71a.

Cross bar 71a could also be attached to the lever arm. Although the arm motion would trace an arc, cutting could be effectively accomplished even though wider tolerances might be required. One of the added benefits of this approach would be that the blades could be withdrawn with the lever arm, allowing the upper portion of the blades to be solid and also allowing them to be fitted with an outer annular shoulder that could be brought into sealing communication with the septa shoulder about where the core was removed. Because the blades are solid and do not have a through bore in this case, when forming a seal with the septa shoulder it would facilitate resealing and repressurizing of the housing internal cavity at some time after coring should that be desired. Inserts 197 and 43a in the flanged septa 44 and 190, respectively would add structural rigidity against which the outer annular shoulders of the blades could seal. Lastly, cores could be captured and removed from interfering with operations by including barbed pre-puncture needles mounted in the center of the coring blades. The needles would puncture the septa before being cored and the barbs on the needles would retain and withdraw cores after being cored as the lever arm is rotated back out of the way.

Many other methods for coring the septa are possible. The selection and description of these particular methods are not intended to limit the range of devices for coring that could be used with this device. These methods and descriptions are only intended to be illustrative of some methods for gaining access to the unfilled receptacles and for gaining access for filled receptacles to the empty receptacle sacks.

Conveying the Receptacle Through the Device:

Within the main housing 2 is a means for conveying the unfilled receptacle 51 up from the injection port 30 to the unstoppering station, the filling (and fixing) station, the restoppering station down through the ejection port 170. This device for conveyance may consist of a single device or system or a set of systems (subsystems) working in cooperation to convey the receptacle 51 into the main housing 2 to the various stations and back out of the main housing 2. To illustrate the concept, two embodiments are described below. These embodiments are chosen as examples and are merely representative of two of the many methods by which the receptacle could be conveyed into, through and back out of the main housing 2. It should be noted here that device 1 may be designed so that receptacles 51 are supplied from and supplied to a ridged or semi-ridged magazine 40a and 200a or flexible walled package 40 or receptacle tube sack assembly 190. Furthermore, the supply and destinations of receptacles could be located within the housing itself. The disadvantage of this approach is the larger space necessary to house the receptacles within housing 2 and, without additional features such as a transition port, access to filled receptacles would only be possible when the device is opened.

1. Embodiment of Conveyance Device: A Set of Systems (or Subsystems) Working in Cooperation:

Staging Clip Assembly:

Once package septum core 44b is severed from flanged package septum 44, the first receptacle 51 in the series illustrated in device 1 is intended to be manually fed up into internal cavity 2a of main housing 2 until stopper 53 affixed to receptacle 51 is engaged by spring-loaded staging clip assembly 80 and captured. If receptacle 51 were not the first receptacle, the receptacle preceding it in the train would be pulled into the housing by the receptacle conveyance system 50 which would, in turn, pull receptacle 51, attached to the preceding receptacle 51 by the combination thread 59 and tip 58 to sprue 56, cavity 57 and opening 57a up into internal cavity 2a of main housing 2 until its stopper is captured by staging clip assembly 80. As receptacle 51 moves up, the rest of the attached receptacles in the train within receptacle package 40 would also move up. As receptacle 51 is captured and held at the staging clip assembly 80, receptacle conveyance system 50 pulls on its predecessor until tip 58 is pulled free from cavity 57 and opening 57a of stopper 53 or thread 59 breaks or is otherwise cut. It should be noted that stopper 53 and receptacle 51 could be molded as one piece, joined by thread 59 with the intention that thread 59 be broken or cut by an element of the staging clip assembly 80 or receptacle conveyance system 50 as one receptacle 51 is held while its predecessor advances through device 1.

Staging clip assembly 80 has a detent 83 designed to capture receptacles 51 by the stopper 53 as they rise. Staging clip assembly 80 could be modified to capture many other sizes and designs of receptacles or exchanged for other assemblies. The assembly could, in fact, be modified or changed to one which more encircles and confines the movement of the receptacles into the housing. Versatility is the reason that staging clip assembly 80 is removably mounted on pedestal 81.

Staging clip assembly 80 includes angled arms 82 and 84 designed to cause the clip to be deflected to the side and release the receptacle stopper 53 as the receptacle clasp assembly 100 engages and captures the receptacle 51.

Receptacle Conveyance System:

The receptacle conveyance system 50 is illustrated in FIGS. 2A and 2B. In general terms, the system captures the unfilled receptacle 51 from staging clip assembly 80 at the opening of the injection port 30, moves the unfilled receptacle 51 up to the stopper clasp assembly 140 where the stopper 53, if present, is removed, Receptacle conveyance system 50 then moves the open empty receptacle to the opening 6 of supply 5 where it is filled. After being filled, the receptacle 51a is brought back up to be restoppered by the stopper clasp assembly 140 before receptacle conveyance system 50 moves the filled, stoppered receptacle 51a back down and over to the ejection port 170. There the receptacle clasp 100 disengages the receptacle 51a , allowing it to slip down into ejection port 170. If the receptacle 51a is stoppered, the ejector rod tip 160a may engage the top of the stopper 53 before, during or after the receptacle clasp 100 releases the receptacle 51a into the ejection port 170. In any case, the ejector rod 160 can be used to help manipulate the receptacle 51a down through the ejection port 170 into a receptacle tube sack assembly 190 (if employed) and out of the device 1. If tube sacks are used, after the filled receptacle 51a clears the bottom of the ejection port assembly, a seal or closure 188 may be formed along the tube wall 193 using a variety of devices for sealing or closing 189, thereby cutting off communication between environment in the sealed or closed portion of the tube wall 193 containing filled receptacle 51a and the internal cavity environment of the main housing 2. At the same time, the integrity of the environment around the filled receptacle 51a within the section of tube wall 193 and the integrity of the environment within the main housing 2, is maintained both separate and isolated from that of the outside ambient environment. A detailed description of the operation of the conveyance system 50 follows.

As illustrated in FIG. 2B and as described earlier, staging clip assembly 80 captures the stopper 53 of the stoppered unfilled receptacle 51 in detent 82 and holds it.

Handle 101a, located outside main housing 2, is mounted on one end of the manipulator rod 101 and receptacle clasp assembly 100, located inside the internal cavity 2a of the main housing 2, is mounted onto the other end of the manipulator rod 101. Thus, receptacle clasp assembly 100 can be raised and lowered vertically and rotated 360° from the outside by doing the same with handle 101a. As mentioned above, manipulator rod 101 extends up through bore 16 in lower extension 19 and cover plate 3. It is sealed to the outside by combination o-ring 135 and o-ring groove 136 located in the lower portion of extension 19.

Using handle 101a, receptacle clasp assembly 100 can be brought down and into engagement with the side of unfilled receptacle 51, below stopper 53. Receptacle clasp assembly 100 includes clasp arm 102a, linear bearing arm 102b, liner bearing 104, spring loaded clasp arms 102c, spring arms 110 and 111, grip rods 114a–114d and grip sleeves 118a–118d.

Clasp arm 102a is mounted directly onto the base of manipulator rod 101 and has a rear extension. Linear bearing arm 102b houses linear bearing 104 which is mounted on subassembly alignment rod 105. Alignment rod 105 is fixed onto stopper clasp assembly 140. This arrangement permits receptacle clasp assembly 100 to slide freely up and down subassembly alignment rod 105, independent of vertically fixed stopper clasp assembly 140 but which cause the two assemblies to be in locked rotational position relative to each other so that, as receptacle clasp assembly 100 is rotated, stopper clasp assembly 140 rotates by the same amount. As a result, any receptacle 51 or stopper 53 held by either always maintains their relative rotational alignment, regardless of position.

In addition, two spring-loaded clasp arms 102c are fitted with vertical grip rods 114a–114d to grip the side of the receptacle. In order to improve gripping capability on very smooth and wet receptacles, these rods may be covered with grip sleeves 118a–118d designed to enhance the clasp's ability to grip the receptacle. Sleeves with elastomeric, adhesive or abrasive exteriors are examples of materials that may aid gripping. For instances where stopper removal includes the application of strong rotational forces, vertical grip rods prove much more effective than radial grip rods. This is because a vertical grip rod would wipe across a wide exposed area of the receptacle at one time as opposed to other approaches such as radial grip rods that would not. Spring arms 110 and 111 or similar tensioners may be added to provide added pressure on the grip rods to improve gripping.

Receptacle clasp assembly 100 can be moved down and/or rotated around near base plate 4 so as to engage wedge-shaped release jams 109 (not visible in FIG. 2) located adjacent to injection port 30 and ejection port 170 at the junction of the two spring loaded clasp arms 102c, forcing them apart to facilitate grasping or releasing receptacle 51.

Captured receptacle 51 with stopper 53 in place can be raised vertically so that stopper 53 is engaged and captured by stopper clasp assembly 140 by raising handle 101a vertically. Stopper clasp assembly 140 includes clasp body 121, clasp gear 121a, main gear 121b, grip rods 141a–141d, grip sleeves 145a–145d, cam 133 with lobe 139 and its bore 139a and lobe 131 with its bore 131a, upper pinion 122a and lower pinion 122b. The grip rods 141a–141d are attached to clasp body 121, are slightly tapered and may be tension mounted so as to receive the stopper 53 and hold it firmly as it is forced up between the rods on top of the receptacle 51. As with receptacle clasp assembly 100, these rods may include grip sleeves 145a–145d to assist in tightly securing stopper 53 when it is engaged. Clasp gear 121a is nonrotatingly fixed to clasp body 121 by lower pinion 122b. The Clasp body 121, clasp gear 121a, grip rods 141a–141d and sleeves 145a–145d are all attached as one rotatable element cam 133 by means of upper pinion 122a positioned in bore 131a of lobe 131 of cam 133. Bore 137 of cam 133 is mounted rotationally free in recess 138 of lower extension 19. Subassembly alignment rod 105 is fixed into bore 139a of lobe 139 of cam 133. As described earlier, fixing the position of subassembly alignment rod 105 on cam 133 forces receptacle clasp assembly 100 to remain in fixed rotational alignment with stopper clasp assembly 140 attached to cam 133. Main gear 121b is fixed to the wall 2b of internal cavity 2a of main housing 2. With cover plate 3 in place, main gear 121b is fixed in the same horizontal plane as clasp gear 121a so that the two always remain meshed. If handle 101a is rotated, receptacle clasp assembly 100 and stopper clasp assembly 140 both rotate about manipulator rod 101. Because clasp body 121 and its fixed parts are also fixed to clasp gear 121a which is meshed with main gear 121b, besides causing receptacle clasp assembly 100 and stopper clasp assembly 140 to rotate, turning handle 101a will also cause clasp gear 121a and clasp body 121 and its associated fixed parts to spin on their own axis about upper pinion 122a. With receptacle 51 captured in receptacle clasp assembly 100 and stopper 53 captured in stopper clasp assembly 140, rotating handle 101a in one direction will cause a threaded stopper 53 to unscrew from the receptacle being held fixed on its own axis in the receptacle clasp assembly 100 while rotating handle 101a in the other direction would cause it to thread back on to the receptacle 51 or 51a. In this way stoppers 53 may be removed and reattached to receptacles 51 or 51a. Spring loaded clasps in combination with the rotational motion of either the stopper 53 or the receptacle 51 or 51a relative to the other in combination with applied vertical pressure is the commonly used method for opening stopper-receptacle combinations, even if they are friction tight and not held by threads.

In the manner described above, a receptacle 51 may have the stopper 53 temporarily removed. With the stopper 53 removed, handle 101*a* can be used to rotate and position the mouth 52 of the receptacle 51 under openings 6 and 8 of supplies 5*a* and 7*a*, respectively, or any other supply opening into internal cavity 2*a*. Once filled, handle 101*a* may again be used to maneuver filled receptacle 51*a* into communication with the stopper 53 still held in stopper clasp assembly 140 by, first, rotating receptacle 51*a* out from under openings 5*a* and 7*a* and then raising the receptacle clasp assembly 100 until the top of the receptacle 51*a* mates with the bottom of the stopper 53. Rotating handle 101*a* in the opposite direction as before will reattach stopper 53.

Filled, stoppered receptacle 51*a* may be rotated so that it is over ejection port 170 and lowered down into it. Filled receptacle 51*a* may be dislodged from receptacle clasp assembly 100 by rotating receptacle clasp assembly 100 in the direction opposite the opening in the clasp while the lower half of the receptacle 51*a* is in the ejection port, by mating the clasp arms 102*a* with the release jam 109 adjacent to ejection port 170, by pressing down on the top of stopper 53 with ejector rod 163 or some combination of the above. Once dislodged, receptacle clasp assembly 100 may be rotated back to a position ready to capture the next unfilled receptacle 51 and the process begins again.

Gravity may be sufficient to move filled receptacle 51*a* through ejection port throughbore 170*a* however, as mentioned above, ejector rod 163 may also be used.

Ejection Port Assembly:

Ejection port 170 has the same general arrangement as injection port 30. The rejection port 170 includes an outer tubular section 171 that extends down beyond the bottom of base plate 4 and is shown terminating in a sanitary clamp flange 173. Ejection port through bore 170*a* is counterbored from the bottom to form counter bore 171*a* terminating at the top in seal face 174 with a relieved outer annular edge forming alignment recess 175 so that the internal bore of tubular section 171 is flush internally with the outside diameter wall of alignment recess 174.

Like injection port 30, ejection port 170 also has an insert 177 whose forward or upper portion 177*a* nests inside the inner bore of tubular section 171 which has a seal face 178 also with a relieved outer annular edge forming alignment recess 179. Insert 177 is also shown with a sanitary clamp flange 176 to mate with flange 173 of tubular section 171, much as injector port 30 does. A sanitary clamp 172 fits over flanges 173 and 176 to hold them together. Many methods may be used to secure mating elements together. The flange clamp combination shown here is used only by way of example. Many other combinations may be employed, including bolt flanges, threaded collars, etc.

Although insert 177 could be substantially the same length or even shorter than insert 32, FIGS. 2C and 2D show a tubular extension 177*b* on insert 177 that extends substantially further down and which terminates with an external threaded portion 177*d* and, interiorly, in a truncated conical opening 177*c*. External threaded portion 177*d* may receive a threaded blind end cap 201 to protect the exposed blind end of receptacle tube sack assembly 190 that will be discussed below.

Tube Sacks or Filled Receptacle Holder:

FIGS. 2A–2D illustrates a device that is designed to allow filled receptacles 51*a* to be removed from the device 1 as single unit receptacles, multiple receptacles as a single group or multiple receptacles as individual receptacles all without losing the integrity of the environment around the receptacle (or receptacles) and without losing the integrity of the environment within the device 1. This may be accomplished by attaching a length of empty blind ended sealed tubing constructed similarly to the receptacle package already described (except without any receptacles), allowing access to be gained into one end of the blind tube, the end with the septum, by the same coring means described earlier for the receptacle package, thereby opening the interior to receive filled receptacles as they are ejected through the ejection port 170. Although illustrated in FIGS. 2A–2D as a soft sided tubular structure, like the receptacle package, the tube sack or filled receptacle holder may also be constructed as a semi-ridged or ridged container or magazine. Also like the receptacle package, rather than a septum, the access into the structure might also be structured in other ways, such as a valve.

As the first filled receptacle 51*a* is fed out of the ejection port 170 into the receptacle tube sack assembly 190, whether rolled, folded or pleated, the first length of tube wall 193 that has been sealed at the distal end to form a blind length of tube sack, the blind end tube sack 191, can be fed out. After the portion of the blind end tube sack 191 with the filled receptacle extends out beyond the lower conical portion 177*c*, the sack may be sealed in single or multiple seal fashion, segregating the internal environment of the housing from that within the length of blind end tube sack 191 now containing filled receptacle 51*a* to form a compartment. Before the length of tube wall 193 is sealed; however, an agent may be added into the length of blind end tube sack 191 now containing filled receptacle 51*a* to protect, stabilize, clean, sterilize, neutralize or otherwise decontaminate or treat the material still on the outside of the receptacle 51*a* and any residing within the blind end tube sack 191. With the filled receptacle 51*a* in the blind end tube sack 191 a seal or closure 188 may then be made by a device for sealing or closing 189. This device could be any appropriate means, including twisting, crimping, heat sealing, sonicating, gluing, tieing-off, zipping, clamping or any other pressure, temperature, chemical, physical or biological device. Furthermore, the seal or closure 189 could consist of single or multiple seals or closures formed in between sections of tube wall used to form a blind end tube sack 191 to receive the next filled receptacle 51*a*. It should be noted here as stated elsewhere in this disclosure that agents may be added into the sections of tube wall between seals of closures or into the section where a seal or closure will be made in order to promote cleaning, sterilizing, neutralizing, decontaminating or otherwise treating the material in that area so that when the tube wall is cut through to separate the distal sealed or closed section of tube wall containing the filled receptacle from the section of tube wall ending in a blind end tube section still attached to the device, material or residue won't be released into the outside ambient environment.

Whether or not an agent is added, the sealed sack containing the filled receptacle may be separated from the remaining sealed blind end section of tube sack still attached to the device. Ends of the cut tube wall may be treated after cutting as well in order to further limit the exchange of the contents with the ambient environment. Seals along the tube sack may be formed in many ways, including, but not limited to zip locks, heat sealing, tying off and crimping. A detailed description of other aspects of removing and detaching the filled receptacle from the device follows.

Referring again to FIGS. 2A–2D, tube wall 193 is shown as being a flexible tubular structure with a straight, folded, rolled, pleated or nested tube wall with an interior space or lumen 193a. The distal end of tube wall 193 is sealed or closed to form a blind end while the end proximal to the device 1 is shown fused into the bottom of flanged sack septum 195 at a position radially inward from the bottom annular sealing surface 193c (annular sealing surface 193b being the top sealing surface). Also fused to the bottom of flanged sack septum 195 and extending downward but positioned slightly radially inward is sack support cylinder 196. When cored, the bore through flanged sack septum left after it has been cored, called septum bore throughhole 190c, opens into the lumen 196a of sack support cylinder 196 so that, when a filled receptacle 51a is expelled through ejection port 170, it passes through lumen 196a. Sack support cylinder 196 is not required but does keep tube sack 191 from collapsing and, since sack support cylinder 196 terminates proximally to truncated conical section 177c, it helps to control the playout of tube sack 191. Tube sack 191 is therefore, positioned in the space between the outside wall of sack support cylinder 196 and the inside wall of insert 177.

Flanged sack septum 195 is captured in the upper portion of ejection port 170 in the same manner as flanged package septum 44, as can be seen in FIGS. 2A–2D.

Figure 6:
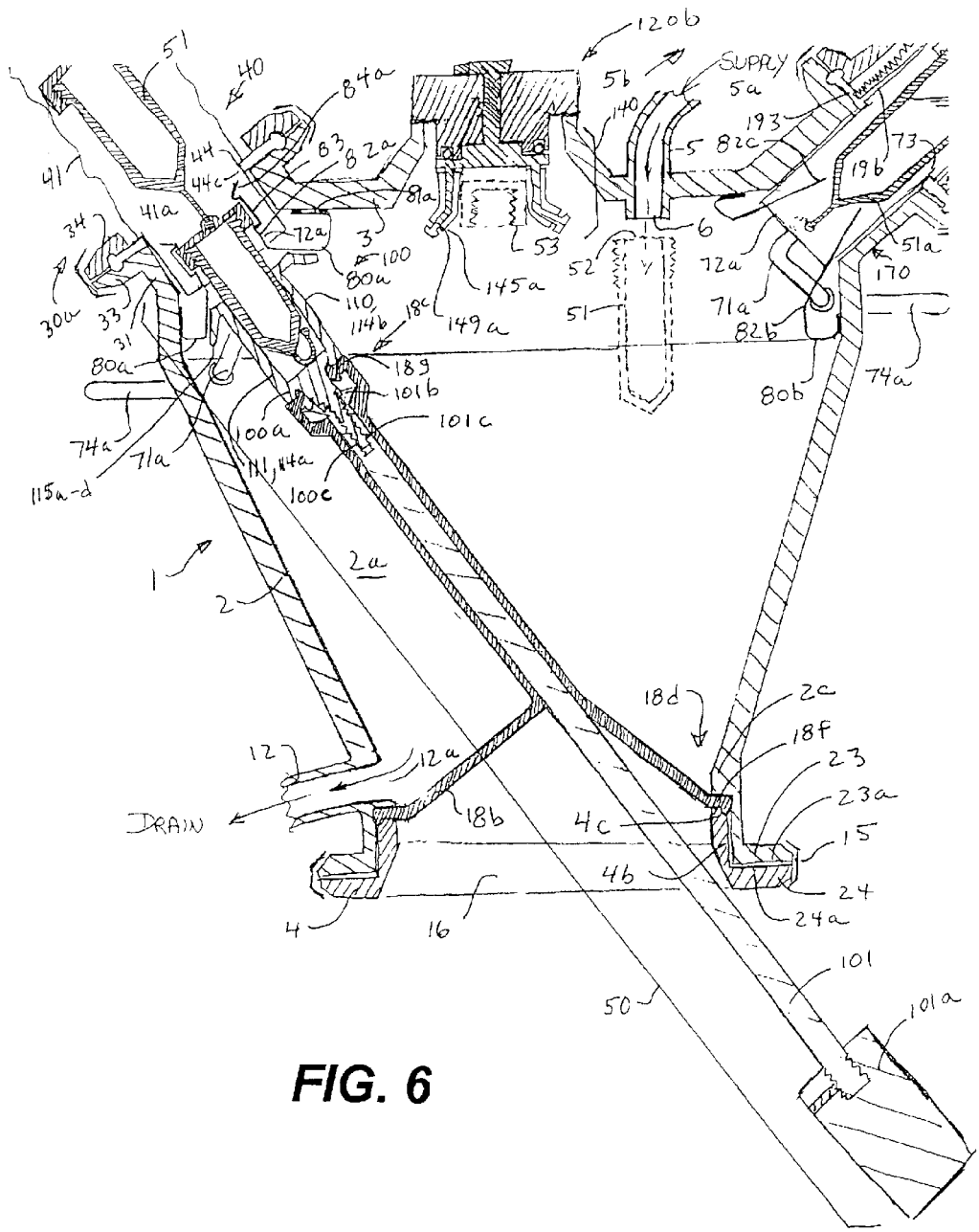
FIG. 6 is a vertical cross section of an alternative embodiment of the device of the present invention, wherein all of the operations of the first embodiment may be accomplished with a single manipulator mechanism.

2. Embodiment of Conveyance Device: A Single Device or System:

FIG. 6 shows an embodiment of the device in which a single arm mechanism, working in cooperation with a reversible ratchet equipped stopper clasp, can destopper thread stoppered receptacles, fill the receptacle, restopper the receptacles and place the receptacles in the ejection port 170 as described earlier. One of the benefits of this arrangement is that the arm mechanism is completely isolated from the internal environment within the housing by a flexing (up/down and rotating) necked conical diaphragm 18b. The neck portion allows for most of the rotational movement while the neck and cone section combine to provide the up/down movement. While this embodiment shows coring of the injector septum and the ejector septum performed by two separate arms 74a, the action could be performed by a single arm. In either case, these coring devices could be equipped with flexing diaphragms to isolate the source of motion outside the housing from the action of the motion within the internal cavity of the housing.

Another feature of this embodiment is the reversible ratchet equipped stopper clasp to destopper and restopper receptacles. While the function could be performed by a fixed position stopper clasp in combination with the flexing, rotating necked conical diaphragm (thus eliminating any seals associated with the ratchet mechanism), this ratchet mechanism allows unlimited rotation in either direction without the need to first disengage and reengage the stopper from the clasp. Like other rotation devices capable of unlimited rotation in a direction, a significant amount of rotation in one direction limits the seal from the possibility of being a twistable sleeve or diaphragm to one that must allow sealing against a freely rotating surface, such as in the case of o-rings, bushings or other mechanical-type seals, all of which do not provide the level of isolation that a sleeve or diaphragm is capable of. The system integrity loss risk associated with the ratchet mechanism may be limited; however, by placing the portion of the ratchet with unlimited rotational capabilities within the housing while allowing communication through more effective flexing isolating seals (of diaphragm type, for instance) to easier-to-seal limited rotational portion components such as the directional switch mechanism to the ratchet.

The injection and ejection ports in FIG. 6 both include staging clip assemblies 80a and 80b, two in each case. Furthermore, while the staging clip assemblies shown in the injection port 30a function similarly to that shown in FIGS. 2A–2D, they extend up into the injection port. Also, those shown on the ejection port 170 do not include detents but, rather end with straight edges 82c or edges that tend to grip the sides of the receptacle and inhibit its being pulled back into the main housing 2 as the receptacle clasp is pulled back into the main housing 2 in order to clasp the next unfilled receptacle. That receptacle, once captured, can be used to assist the ejection of the previous filled receptacle by pushing it from behind.

This embodiment can perform the same functional operations as the embodiment of FIGS. 2A–2D described above. As mentioned in the description of the embodiment in FIGS. 2A–2D, a cover plate 3 or base plate 4 can be attached to the main housing 2. Furthermore, as mentioned previously, components shown located in cover plate 3 or base plate 4 could be switched or combined into one plate or the other. As such, receptacle injection port 30 and receptacle ejection port 170, shown installed in base plate 4 in FIGS. 2A–2D are now shown installed as a part of the new fixed cover plate of FIG. 6. Also, receptacle conveyance system, formerly shown located through cover plate 3 in the embodiment of FIGS. 2A–2D is now shown installed through base plate 4 in the embodiment of FIG. 6. Because the receptacles need to be re-stoppered in the up-right condition, stopper clasp assembly 140 remains located in the upper portion of the housing. Likewise, because drainage flows down, drain port 12 and its opening 12a remain located in the lower portion of housing 2. Whereas manipulator rod 101 with its attached receptacle clasp assembly 100 was shown entering through a o-ring groove seal combination (135, 136) located in cover plate 3 in the previous embodiment, In FIG. 6, it is shown entering through base plate 4 through a different type of seal; specifically, a necked conical diaphragm seal 18b with two parts, upper portion 18c and lower portion 18d. The outer radial lip 18f is captured between the top surface 4c of an upper tubular extension 4b of base plate 4 and a top face 2c of a counter bore up into side wall 2b of main housing 2. Upper seal 18c of necked conical diaphragm seal 18b is formed by the capture of the radially inward extension of lip 18g between a lower surface 100a of receptacle clasp assembly 100 and an upper surface 101b of manipulator rod 101. While lip 18f is shown being captured through the attachment of clamp 15 onto flanges 23 and 24, the seal at lip 18g is shown being created when male threaded section 100c of receptacle clasp assembly 100 is threaded down into a female threaded section 101c of manipulator rod 101. The mating of flanges under a clamp and the mating of threads are two ways described by way of example that the seals 18c and 18d may be formed. Many other arrangements are possible for these seals and these would be known and understood by one knowledgeable in the art and, now that the concept has been described, should be considered as being included within the scope of this description.

In FIG. 6, as in FIGS. 2A–2D, receptacle clasp assembly 100 is shown attached to the end of manipulator rod 101 and assembly 100. It includes spring arms (110, 111) as well as grip rods 114a–d which may, again, be covered by grip sleeves 18a–d. The assembly, however, is shown as being mounted so as to be a direct linear extension of manipulator rod 101. By mounting the assembly thus, if a rotary motion is necessary to remove or attach a stopper, the rotary motion must come from either rotation assembly 100 by means of manipulator rod 101 in combination with a fixed stopper manipulator assembly (not shown) equipped with a fixed stopper clasp assembly (not shown). The device shown in FIG. 6 is equipped with a stopper manipulator clasp assembly 120b capable of rotary motion by means of a reversible-direction ratchet mechanism 140b. While rotary motion in this case is still supplied by rotation of the manipulator rod, the total range of rotation capability required of the manipulator rod is limited to increments with the assistance of the ratchet mechanism. It is also possible to equip the device with more sophisticated ratchet mechanisms that are self-rotating, thus eliminating the need for the manipulator arm to be rotatable at all.

FIG. 6 illustrates another arrangement of staging clip assembly 80, staging clip assembly 80a, where the angled arms 82a and 84a are recurved and extend up into receptacle injection port throughbore 30a. The detent 83 is the same but pedestal 81 is shown reduced, and identified as pedestal 81a in FIG. 6. Angled arms 82a and 84a can be caused to retract and release captured stopper 53 by the recurved extensions of grip rods 114a–d, clip release arms 115a–d. This can be accomplished when manipulator rod 101 and receptacle clasp assembly 100 are pushed up to capture an unfilled receptacle 51 and, at the same time, force angled arms 82a and 84a apart.

Receptacle ejection port 170 in FIG. 6 is also shown with a clip assembly 80b designed to allow the filled receptacles to be extricated from the receptacle clasp assembly 100 as it is retracted from delivering the filled receptacle into receptacle ejection port 170. This clip assembly 80 is equipped with angled arms 82b, which terminate in an edge 82c designed to grip the outside of the receptacle.

FIG. 6 also illustrates a modified version of coring assembly 70, coring assembly 70a, in which the receptacle injection port and the receptacle ejection port both have their own coring assembly 70. Each assembly includes a bent coring rod handle 74a, which is fitted rotatably through side wall 2b of housing 2 and attached, rotatably, to a cylindrical blade 72a. As with the angled arms of staging clip assembly 80a, these blades also extend further into the ports in order to show that the function of the device may still be performed even thought the these ports may be formed in many different ways.

It also should be noted that in the embodiment shown in FIG. 6, the cover plate is formed as a part of main housing 2 with receptacle injection port 30 and receptacle ejection port 170 located at the lateral margins. As mentioned above, elements of the system may be modified and reoriented without losing the functionality of the system so long the receptacles can be received, manipulated, have material collected in them and then have them transferred or made ready to be transferred from the device.

As with the device illustrated in FIGS. 2A–2D, the device shown in FIG. 6 can be used with single receptacles, unprestopper receptacles, receptacles using other types of stoppers than threaded ones as well as many other types of stoppered and non-stoppered arrangements.

FIG. 7 through 11 illustrate how a stoppered receptacle can be filled into a single tube sack. FIGS. 7 and 8 illustrate that the tube sack need not cover the entire receptacle stopper combination.

FIGS. 7 and 8 illustrate one example of many types of possible stopper-receptacle arrangements that could be used. In this case, the stopper consists of two parts, threaded cap 53a and plunger 53b. This arrangement could be supplied in the plunger up or down condition and could be used in any of the embodiments presented (including that of FIG. 9, if supplied in the plunger up condition). Material can be supplied through the bore 53c in the plunger 53b. Once filled, the plunger can be depressed and held in place by one of the sets of ribs 53d.

FIGS. 7–9 all illustrate embodiments of the device wherein a receptacle is equipped with an individual receptacle tube sack which will allow that receptacle to be removed from a dedicated receptacle filling station, either through the cover of the device or through the base of the device. If removed through the cover, the receptacle is pulled up causing the tube sack to be pulled down around the materials-exposed areas. The tube sack can then be closed and/or sealed below, thereby enclosing the exposed surfaces within the tube sack. If the receptacle is removed through the base; however, its removal causes the receptacle tube sack to be pulled up over the material-exposed surfaces. The tube sack can then be closed and/or sealed over the material-exposed areas.

One of the benefits of the stopper arrangement in FIGS. 7 and 8, particularly when the plunger 53b is supplied in an opened state, either as a package of many or as a single unit as shown FIG. 7, is that no threading mechanism is required to seal the receptacle after filling, only a ram plunger mechanism. While the one depicted in FIG. 7 is o-ring sealed, the seal could also be a flexing diaphragm or sleeve which, although not as long lived or able to withstand the stresses of high pressure operation, would provided a greater degree of sealing effectiveness.

There are many possible receptacle designs and FIG. 7 also illustrates another receptacle design wherein material may be filled into it and it may be closed without requiring rethreading a cap onto the receptacle. While in this case illustrated in this figure the plunger is shown installed in a threaded cap, it could also be installed into a fixed top or even onto the vertical sidewalls of the receptacle.

FIG. 7 also illustrate how an individual receptacle may be equipped with its own dedicated tube sack, allowing it to be removed from the device individually while preserving the environment of the filling areas immediately around the receptacle and within the housing largely separate from that of the surrounding ambient environment;

FIG. 8 illustrates the filled, sealed receptacle with the tube sack sealing over a top of the plunger stopper/threaded stopper combination but not over the receptacle itself. In this case the filled receptacle is removed down. In FIG. 9; however, an arrangement is illustrated in which the tube sack is attached to the top of an individual stopper (as also was the case in FIGS. 7 and 8 as opposed to the independent multiple tube sack arrangements of FIGS. 1A–2D, 5 and 6) wherein the individual filled stoppered receptacle is removed upward and, in this case, the stopper and receptacle combination would both be captured within the tube sack once it was sealed (not shown sealed). In each case the housing is left with the other portion of the tube sack that has the flange. It is important to note that this portion also has a blind seal so that the integrity of the internal housing environment is maintained and the materials released into the housing during the receptacle filling operation also contained and kept isolated from the surrounding ambient environment. By so doing the housing can be recapped and internally cleaned, sterilized, neutralize or otherwise decontaminated before being reopened to the ambient environment and refitted with another unfilled receptacle.

FIGS. 10a and 10b illustrate a tube sack with ring or dot shaped pouches. These pouches may be filled with an agent that can be released into tube sacks once the filled receptacle is sealed within the sack. The agent could be a neutralizing, sterilizing, decontaminating or any other type of desirable agent. Furthermore, the pouches may be positioned between double seals in cases where the process of sealing itself may not effectively neutralize the materials present within the sack, receptacle or housing so that when a cut is made across the middle of the seal those exposed ends may release undesirable materials. Also, a seal may be made across the pouches so as to entrain agent into the seal.

Because any area within the tube sack will contain residue of material filled into the receptacle (because the internal surface of the tube sack was also exposed to the housing's internal environment where the filling operation was performed), a first unbroken seal may be made in the tube sack above the filled receptacle (or below, if the receptacle is removed through an upper port) before a cleaning, sterilizing, neutralizing or otherwise decontaminating agent is added into the tube sack. A second unbroken seal may then be made above the reservoir of added agent thereby segregating the agent containing area into a pouch within the tube sack, between the portion of the tube sack holding the filled receptacle and the portion still connected and exposed to the environment within the housing. After allowing the agent to work, the portion of the tube sack containing the filled receptacle may be removed from that still connected to the housing by cutting through the now decontaminated pouch. The second concept is that of preincorporating the agent into the structure of the tube sack, shown here as annular pouches. FIG. 10B also illustrates how the decontaminating agent may be added into the portion of the tube sack containing the filled receptacle so as to act on residue within that environment before it is opened. The agents also could be added into the housing for the same purposes.

Figure 11:
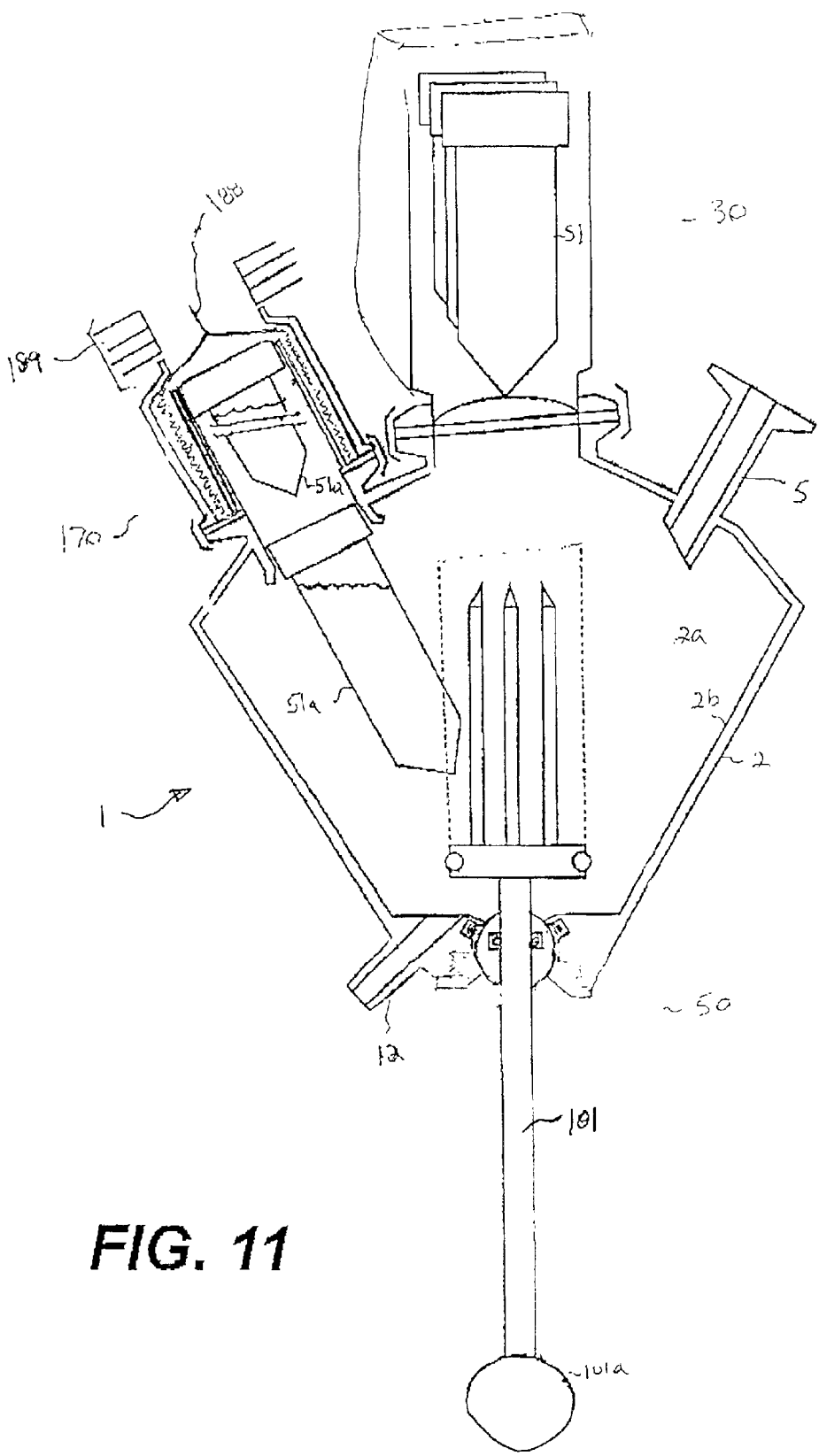
FIG. 11 is a cross-section of an alternative embodiment of the present invention.

FIG. 11 illustrates the basic elements of yet another embodiment of the device, as well as a sealing device necessary for sealing the tube sack as a filled receptacle is withdrawn and segregated from the internal housing environment.

The information contained herein will make many other combinations and permutations of the embodiments apparent to one knowledgeable in the art. These combinations and permutations are, therefore, considered part of this disclosure and are covered by the claims that follow. Some of the alternatives of the present invention which should be considered as a part of the present invention are as follows.

For example, although o-rings may be deemed insufficient to seal sliding and/or rotating shafts in some instances, the shafts of the system according to the present invention can be equipped with elastomeric sleeves which include a first static seal anchored to the housing and a second static seal anchored on a corresponding shaft. This will allow the shafts to be slipped and/or rotated while maintaining an absolute seal between the inside of the housing and the surrounding outside environment.

In addition, the system may be automated.

Although the embodiment of the present invention is directed to receiving a sealed container containing one or more precleaned and/or presterilized receptacles, the device of the present invention can accept non-precleaned and non-presterilized receptacles and that are supplied into the system from a non-sealed container.

Although the embodiment of the present invention is directed to filling multiple receptacles, the device can be used to fill single receptacles.

Although the embodiment of the present invention is directed to filling receptacles without losing the integrity of the system, filling can be performed within the system while it is opened to the outside environment Although the embodiment of the present invention is directed to stoppering receptacles after filling, the system can be used to fill receptacles only, without stoppering them before releasing them Although the embodiment of the present invention is directed to the more complicated situation of first requiring the removal of screwed on caps from individual receptacles before filling them, it should be understood that the simpler case of supplying receptacles for filling with non-screwed on caps or un-stoppered receptacles would be within the present invention, since a simpler situation than that of the more demanding capture, unscrewing and separation of the cap from the receptacle before filling can be accomplished with the device according to the present invention.

Although the embodiment of the present invention is directed to the more complicated situation of re-stoppering receptacles with screwed on type stoppers after filling, it is understood that the simpler case of re-stoppering with non screwed on type stoppers or not restoppering at all after filling would be within the present invention, since this presents a simpler situation than that of the more demanding re-mating of a threaded cap with a threaded portion of the receptacle.

Although the embodiment of the present invention is directed to the release of the filled receptacle into a sack or container that can be sealed against the surrounding environment, allowing maintenance of the internal integrity of the device and that these seals may be single or multiple in nature, it is understood that the simpler case of providing over pressure to the system using purified (higher quality than the ambient) air or the still simpler situation of providing no barrier between the interior of the device of that surrounding the receptacle would also be within the present invention.

Although the embodiment of the present invention is directed to receiving receptacles from a container outside of the device, a reservoir of receptacles could be harbored within and supplied for filling from within. In this case, not having to provide a system to introduce the receptacles into the system would tend to simplify the device of the present invention. Furthermore, since the receptacles would then be housed within the system, they could be cleaned and/or sterilized in place, thereby further simplifying the system.

The description of this device also mentions the possibility of a fixative being added to the receptacles sometime before they are released to the outside environment. The requirement for the addition of one or more agents into the receptacle should be considered an extension covered by this description. In the same way, the addition of one or more agents into the housing and/or into the sack or container into which the receptacles are placed should be considered direct extensions of the above described fixative addition and should also be covered by this disclosure.

Lastly, each of the motions described may be automated and may be sealed such that exchange between the internal system environment and the ambient environment outside the system are substantially isolated from one another.

The invention being thus described, it will be obvious that the same may be varied in many ways. Such variations are not to be regarded as a departure from the spirit and scope of the invention, and all such modifications as would be obvious to one skilled in the art are intended to be included within the scope of the following claims.

What is claimed is:

1. A device for collecting samples from within a sealed system, comprising:

a housing, said housing having an internal cavity sealed from the ambient environment outside the housing;

a plurality of receptacles, each of said plurality of receptacles being movable into said internal cavity of said housing and fillable with a flowable material while within said internal cavity of said housing, respectively; and a filled receptacle holder, said filled receptacle holder receiving each of said plurality of receptacles after each of said plurality of receptacles has been filled, said filled receptacle holder being sealed with said housing to form a barrier between the environment within said internal cavity of said housing and the ambient environment outside said housing, wherein said filled receptacle holder is an integral tube which is separable into a plurality of filled receptacle compartments, a first of said plurality of compartments having an open end thereof forming a seal with said housing, and a last of said plurality of compartments having a closed distal end, each of said plurality of compartments being closable to contain at least one of said plurality of filled receptacles therein in an isolated manner.

2. The device for collecting samples from within a sealed system according to claim 1, wherein said last of said plurality of compartments is closable after a first of said plurality of filled receptacles is received therein to isolate said first filled receptacle from the environment within said internal cavity of said housing and from said ambient environment outside the housing, remaining of said plurality of compartments remaining in an open condition with said internal cavity of said housing to receive a subsequent filled receptacle therein.

3. The device for collecting samples from within a sealed system according to claim 2, wherein each of said plurality of compartments is closable at opposite ends thereof to isolate adjacent of said plurality of compartments from each other when a respective of said plurality of compartments has received a filled receptacle therein.

4. The device for collecting samples from within a sealed system according to claim 2, wherein each of said plurality of compartments is closable by one of the group consisting of heat sealing, zipper sealing, crimping, adhesive sealing, screw capping, twisting, sonicating, tying off, clamping and stoppering.

5. The device for collecting samples from within a sealed system according to claim 1, further comprising a flowable material supplier, said flowable material supplier being operable to supply a flowable material between adjacent of said plurality of compartments when one of said plurality of compartments has been closed to enclose at least one of said plurality of receptacles therein.

6. The device for collecting samples from within a sealed system according to claim 1, further comprising:

an injection port formed in said housing; and an empty receptacle holder, said empty receptacle holder being in communication with said injection port and being sealed with the housing to form a barrier between the environment within the internal cavity of said housing and the ambient environment outside said housing, wherein said empty receptacle holder holds said plurality of receptacles therein prior to filling within said housing.

7. The device for collecting samples from within a sealed system according to claim 1, further comprising:

a receptacle conveyor, said receptacle conveyor being movable to transport each of said plurality of receptacles to a filling station within said internal cavity of said housing where each of said plurality of receptacles is fillable, respectively and from said filling station to an ejection port formed in said housing; and a flowable material feeder having an opening at said filling station within said internal cavity of said housing, said flowable material feeder being operable to feed material from a supply source into each of said plurality of receptacles.

8. The device for collecting samples from within a sealed system according to claim 7, further comprising a stopper removing or opening mechanism, said stopper removing or opening mechanism being operable to remove or open a stopper from each of said plurality of receptacles when each of said plurality of receptacles is located at said filling station to allow for each of said plurality of receptacles to be filled by said flowable material feeder.

9. The device for collecting samples from within a sealed system according to claim 8, wherein said stopper removing or opening mechanism is operable to remove a screw-on or plug stopper from each of said plurality of receptacles, open a port in each of said plurality of receptacles, or penetrate a septum on each of said plurality of receptacles.

10. The device for collecting samples from within a sealed system according to claim 8, further comprising a stopper attaching mechanism, said stopper attaching mechanism being operable to attach a screw-on or plug stopper to each of said plurality of receptacles, close a port in each of said plurality of receptacles, or close or seal a penetrated septum on each of said plurality of receptacles.

11. The device for collecting samples from within a sealed system according to claim 1, further comprising:

a flowable material feeder, said flowable material feeder being operable to feed material into each of said plurality of receptacles; and a flowable material supplier, said flowable material supplier being operable to supply a flowable material into said filled receptacle holder.

12. A device for collecting samples from within a sealed system, comprising:

a housing, said housing having an internal cavity sealed from the ambient environment outside the housing, said housing including an injection port and an ejection port formed therein;

an empty receptacle holder, said empty receptacle holder being in communication with said injection port and being sealed with said housing to form a barrier between the environment within the internal cavity of said housing and the ambient environment outside said housing, said empty receptacle holder holding a plurality of receptacles therein;

a filled receptacle holder, said filled receptacle holder being in communication with said ejection port and being sealed with said housing to form a barrier between the environment within the internal cavity of said housing and the ambient environment outside said housing, said filled receptacle holder for receiving said plurality of receptacles therein and being removably mounted to said housing such that the environment inside said housing and the environment inside said filled receptacle holder remain sealed from each other and the ambient environment outside the housing when said filled receptacle holder and said housing are removed from each other, wherein each of said plurality of receptacles is movable from said empty receptacle holder into said internal cavity of said housing to be filled with a flowable material while within said internal cavity of said housing, and said plurality of receptacles is movable into said filled receptacle holder to be removed therewith, and wherein said filled receptacle holder is an integral tube which is separable into a plurality of filled receptacle compartments, a first of said plurality of compartments having an open end thereof forming a seal with said housing, and a last of said plurality of compartments having a closed distal end, each of said plurality of compartments being closable to contain at least one of said plurality of receptacles therein in an isolated manner.

13. The device for collecting samples from within a sealed system according to claim 12, wherein said last of said plurality of compartments is closable after a first of said plurality of filled receptacles is received therein to isolate said first filled receptacle from the environment within said internal cavity of said housing and from said ambient environment outside said housing, remaining of said plurality of compartments remaining in an open condition with said internal cavity of said housing to receive a subsequent filled receptacle therein.

14. The device for collecting samples from within a sealed system according to claim 13, wherein each of said plurality of compartments is closable at opposite ends thereof to isolate adjacent of said plurality of compartments from each other when a respective of said plurality of compartments has received a filled receptacle therein.

15. The device for collecting samples from within a sealed system according to claim 13, wherein each of said plurality of compartments is closable by one of the group consisting of heat sealing, zipper sealing, crimping, adhesive sealing, screw capping, twisting, sonicating, tying off, clamping and stoppering.

16. A device for collecting samples from within a sealed system, comprising:

a housing, said housing having an internal cavity sealed from the ambient environment outside the housing, said housing including an injection port and an ejection port formed therein;

an empty receptacle holder, said empty receptacle holder being in communication with said injection port and being sealed with said housing to form a barrier between the environment within the internal cavity of said housing and the ambient environment outside said housing, said empty receptacle holder holding at least one receptacle therein;

a filled receptacle holder, said filled receptacle holder being in communication with said ejection port and being sealed with said housing to form a barrier between the environment within the internal cavity of said housing and the ambient environment outside said housing, said filled receptacle holder for receiving said at least one receptacle therein and being removably mounted to said housing such that the environment inside said housing and the environment inside said filled receptacle holder remain sealed from each other and the ambient environment outside the housing when said filled receptacle holder and said housing are removed from each other, a receptacle conveyor, said receptacle conveyor being movable to transport each of said at least one receptacle to a filling station within said internal cavity of said housing where each of said at least one receptacle is fillable and from said filling station to said ejection port formed in said housing;

a flowable material feeder having an opening at said filling station within said internal cavity of said housing, said flowable material feeder being operable to feed material from a supply source into each of said at least one receptacle;

a stopper removing or opening mechanism, said stopper removing or opening mechanism being operable to remove or open a stopper from each of said at least one receptacle when each of said at least one receptacle is located at said filling station to allow for each of said at least one receptacle to be filled by said flowable material feeder; and a stopper attaching mechanism, said stopper attaching mechanism being operable to attach a screw-on or plug stopper to each of said at least one receptacle, close a port in each of said at least one receptacle, or close or seal a penetrated septum on each of said at least one receptacles, wherein each of said at least one receptacle is movable from said empty receptacle holder into said internal cavity of said housing to be filled with a flowable material while within said internal cavity of said housing, and said at least one receptacle is movable into said filled receptacle holder to be removed therewith.

17. A device for collecting samples from within a sealed system, comprising:

a housing, said housing having an internal cavity sealed from the ambient environment outside the housing, said housing including an injection port and an ejection port formed therein;

an empty receptacle holder, said empty receptacle holder being in communication with said injection port and being sealed with said housing to form a barrier between the environment within the internal cavity of said housing and the ambient environment outside said housing, said empty receptacle holder holding a plurality of receptacles therein;

a filled receptacle holder, said filled receptacle holder being in communication with said ejection port and being sealed with said housing to form a barrier between the environment within the internal cavity of said housing and the ambient environment outside said housing, said filled receptacle holder for receiving each of said plurality of receptacle therein and being removably mounted to said housing such that the environment inside said housing and the environment inside said filled receptacle holder remain sealed from each other and the ambient environment outside the housing, wherein said filled receptacle holder is an integral tube which is separable into a plurality of filled receptacle compartments, a first of said plurality of compartments having an open end thereof forming a seal with said housing, and a last of said plurality of compartments having a closed distal end, each of said plurality of compartments being closable to contain at least one of said plurality of receptacles therein in an isolated manner, and wherein each of said plurality of receptacles is movable from said empty receptacle holder into said internal cavity of said housing to be filled with a flowable material while within said internal cavity of said housing, and each of said plurality of receptacles is movable into said filled receptacle holder to be removed therewith.

18. The device for collecting samples from within a sealed system according to claim 17, wherein said last of said plurality of compartments is closable after a first of said plurality of filled receptacles is received therein to isolate said first filled receptacle from the environment within said internal cavity of said housing and from said ambient environment outside said housing, remaining of said plurality of compartments remaining in an open condition with said internal cavity of said housing to receive a subsequent filled receptacle therein.

19. The device for collecting samples from within a sealed system according to claim 18, wherein each of said plurality of compartments is closable at opposite ends thereof to isolate adjacent of said plurality of compartments from each other when a respective of said plurality of compartments has received a filled receptacle therein.

20. The device for collecting samples from within a sealed system according to claim 18, wherein each of said plurality of compartments is closable by one of the group consisting of heat sealing, zipper sealing, crimping, adhesive sealing, screw capping, twisting, sonicating, tying off, clamping and stoppering.

* * * * *